(12) United States Patent
Houwaert et al.

(10) Patent No.: US 7,770,611 B2
(45) Date of Patent: Aug. 10, 2010

(54) PEELABLE SEAL CLOSURE ASSEMBLY

(75) Inventors: Vincent Houwaert, Mont-St-Aubert (BE); Paul-Andre Gollier, Brussels (BE); Sherwin Shang, Vernon Hills, IL (US); Patrick Balteau, Evelette (BE)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 872 days.

(21) Appl. No.: 11/553,352

(22) Filed: Oct. 26, 2006

(65) Prior Publication Data

US 2007/0144923 A1 Jun. 28, 2007

Related U.S. Application Data

(63) Continuation of application No. 10/792,021, filed on Mar. 3, 2004, now abandoned, and a continuation-in-part of application No. 09/439,826, filed on Nov. 12, 1999, now Pat. No. 7,678,097.

(51) Int. Cl.
*B65B 1/04* (2006.01)

(52) U.S. Cl. .................................. 141/114; 383/38

(58) Field of Classification Search .............. 141/114, 141/9, 100, 104; 383/38–40; 604/87, 90, 604/410, 416; 206/222
See application file for complete search history.

(56) References Cited

U.S. PATENT DOCUMENTS

| 2,714,974 A | 8/1955 | Sawyer |
| 2,907,173 A | 10/1959 | Robbins |
| 3,023,587 A | 3/1962 | Robbins |
| 3,028,000 A | 4/1962 | Clements et al. |
| 3,036,894 A | 5/1962 | Forestiere |
| 3,074,544 A | 1/1963 | Bollmeier et al. |
| 3,113,986 A | 12/1963 | Breslow et al. |
| 3,149,943 A | 9/1964 | Amador |
| 3,190,499 A | 6/1965 | Dow |
| 3,257,072 A | 6/1966 | Reynolds |
| 3,294,227 A | 12/1966 | Schneider et al. |
| 3,324,663 A | 6/1967 | McLean |
| 3,474,898 A | 10/1969 | Montgomery |
| 3,608,709 A | 9/1971 | Pike |
| 3,692,493 A | 9/1972 | Terasaki |
| 3,708,106 A | 1/1973 | Sargent |
| 3,749,620 A | 7/1973 | Montgomery |

(Continued)

FOREIGN PATENT DOCUMENTS

BE 894 377 1/1983

(Continued)

OTHER PUBLICATIONS

International Search Report dated Aug. 23, 2005, 7 pp.

(Continued)

*Primary Examiner*—Steven O Douglas
(74) *Attorney, Agent, or Firm*—K&L Gates LLP

(57) ABSTRACT

The present invention provides a peelable seal for a multi-chambered container including a first edge and a second edge. At least one of the first edge or second edge includes a stress bearing portion and a non-stress bearing portion.

24 Claims, 16 Drawing Sheets

U.S. PATENT DOCUMENTS

| | | | |
|---|---|---|---|
| 3,879,492 A | 4/1975 | Bontinick | |
| 3,950,158 A | 4/1976 | Gossett | |
| 4,000,996 A | 1/1977 | Jordan | |
| 4,226,330 A | 10/1980 | Butler | |
| 4,226,952 A | 10/1980 | Halasa et al. | |
| 4,496,046 A | 1/1985 | Stone et al. | |
| 4,519,499 A | 5/1985 | Stone et al. | |
| 4,608,043 A | 8/1986 | Larkin | |
| 4,629,080 A | 12/1986 | Carveth | |
| 4,770,295 A | 9/1988 | Carveth et al. | |
| 4,798,605 A | 1/1989 | Steiner et al. | |
| 4,961,495 A | 10/1990 | Yoshida et al. | |
| 4,997,083 A | 3/1991 | Loretti et al. | |
| 5,114,004 A | 5/1992 | Isono et al. | |
| 5,128,414 A | 7/1992 | Hwo | |
| 5,139,831 A | 8/1992 | Mueller | |
| 5,176,634 A | 1/1993 | Smith et al. | |
| 5,186,998 A | 2/1993 | Eugster | |
| 5,207,320 A | 5/1993 | Allen | |
| 5,207,509 A | 5/1993 | Herbert | |
| 5,209,347 A | 5/1993 | Fabisiewicz et al. | |
| 5,267,646 A | 12/1993 | Inoue et al. | |
| 5,287,961 A | 2/1994 | Herran | |
| 5,334,180 A | 8/1994 | Adolf et al. | |
| 5,391,163 A | 2/1995 | Christine et al. | |
| 5,423,421 A | 6/1995 | Inoue et al. | |
| 5,462,526 A | 10/1995 | Barney et al. | |
| 5,474,818 A | 12/1995 | Ulrich et al. | |
| 5,482,771 A | 1/1996 | Shah | |
| 5,494,190 A | 2/1996 | Boettcher | |
| 5,509,898 A | 4/1996 | Isono et al. | |
| 5,514,123 A | 5/1996 | Adolf et al. | |
| 5,520,975 A | 5/1996 | Inoue et al. | |
| 5,577,369 A | 11/1996 | Becker et al. | |
| 5,610,170 A | 3/1997 | Inoue et al. | |
| 5,706,937 A | 1/1998 | Futagawa et al. | |
| 5,728,681 A | 3/1998 | Kido et al. | |
| 5,792,213 A | 8/1998 | Bowen | |
| 5,849,843 A | 12/1998 | Laurin et al. | |
| 5,865,309 A | 2/1999 | Futagawa et al. | |
| 5,928,213 A | 7/1999 | Barney et al. | |
| 5,944,709 A | 8/1999 | Barney et al. | |
| 5,967,308 A | 10/1999 | Bowen | |
| 5,998,019 A | 12/1999 | Rosenbaum et al. | |
| 6,004,636 A | 12/1999 | Nicola et al. | |
| 6,007,529 A | 12/1999 | Gustafsson et al. | |
| 6,017,598 A | 1/2000 | Kreischer et al. | |
| 6,024,220 A | 2/2000 | Smith et al. | |
| 6,036,719 A | 3/2000 | Meilus | |
| 6,039,719 A | 3/2000 | Wieslander et al. | |
| 6,039,720 A | 3/2000 | Wieslander | |
| 6,083,587 A | 7/2000 | Smith et al. | |
| 6,117,123 A | 9/2000 | Barney et al. | |
| 6,129,925 A | 10/2000 | Kido et al. | |
| 6,149,655 A | 11/2000 | Constantz et al. | |
| 6,165,161 A | 12/2000 | York et al. | |
| 6,186,998 B1 | 2/2001 | Inuzuka et al. | |
| 6,203,535 B1 | 3/2001 | Barney et al. | |
| 6,231,559 B1 | 5/2001 | Loretti | |
| 6,269,979 B1 | 8/2001 | Dumont | |
| 6,280,431 B1 | 8/2001 | Domkowski et al. | |
| 6,297,046 B1 | 10/2001 | Smith et al. | |
| 6,309,673 B1 | 10/2001 | Duponchelle et al. | |
| 6,319,243 B1 | 11/2001 | Becker et al. | |
| 6,341,802 B1 | 1/2002 | Matkovich | |
| 6,399,704 B1 | 6/2002 | Laurin et al. | |
| 6,468,259 B1 | 10/2002 | Loretti et al. | |
| 6,484,874 B1 | 11/2002 | Kageyama et al. | |
| 6,645,191 B1 | 11/2003 | Knerr et al. | |
| 6,743,451 B2 | 6/2004 | Rasile et al. | |
| 6,846,305 B2 | 1/2005 | Smith et al. | |
| 2001/0000042 A1 | 3/2001 | Inuzuka et al. | |
| 2002/0115795 A1 | 8/2002 | Shang et al. | |
| 2002/0138066 A1 | 9/2002 | Manica et al. | |
| 2003/0047467 A1 | 3/2003 | Smith et al. | |
| 2003/0077466 A1 | 4/2003 | Smith et al. | |
| 2003/0146115 A1 | 8/2003 | Sharp | |
| 2003/0152634 A1 | 8/2003 | Bodmeier | |
| 2003/0160067 A1 | 8/2003 | Gupta et al. | |
| 2003/0194431 A1 | 10/2003 | Miller et al. | |
| 2003/0233083 A1 | 12/2003 | Houwaert et al. | |
| 2004/0078023 A1 | 4/2004 | Gollier et al. | |
| 2004/0134222 A1 | 7/2004 | Holley, Jr. | |
| 2004/0134802 A1 | 7/2004 | Inoue et al. | |
| 2005/0087456 A1 | 4/2005 | Oka et al. | |

FOREIGN PATENT DOCUMENTS

| | | |
|---|---|---|
| BR | 9 905 055 | 6/2001 |
| DK | DE 44 10 876 | 10/1995 |
| DK | DE 691 11 430 | 1/1996 |
| DK | DE 298 14 215 | 10/1998 |
| DK | DE 694 10 351 | 10/1998 |
| DK | DE 198 11 276 | 1/2000 |
| DK | DE 199 03 705 | 7/2000 |
| DK | DE 201 11 308 | 12/2001 |
| EP | 157579 | 10/1985 |
| EP | 0 345 774 | 12/1989 |
| EP | 0 444 900 | 9/1991 |
| EP | 0 513 364 | 11/1992 |
| EP | 0 619 998 | 10/1994 |
| EP | 0 639 364 | 2/1995 |
| EP | 0875231 | 11/1998 |
| EP | 0 920 849 | 6/1999 |
| EP | 0 972 506 | 1/2000 |
| EP | 1 103 487 | 11/2000 |
| EP | 1 101 483 | 5/2001 |
| EP | 1 106 644 | 6/2001 |
| EP | 1 161 932 | 12/2001 |
| EP | 1 350 739 | 10/2003 |
| GB | 2 134 067 | 8/1984 |
| JP | 01-240469 | 9/1989 |
| JP | 04-097751 | 3/1992 |
| JP | 05-068702 | 3/1993 |
| JP | 06-039018 | 2/1994 |
| JP | 07-303694 | 11/1995 |
| JP | 08-100089 | 4/1996 |
| JP | 08-215285 | 8/1996 |
| JP | 08-229101 | 9/1996 |
| JP | 08-280774 | 10/1996 |
| JP | 09-010282 | 1/1997 |
| JP | 09-122205 | 5/1997 |
| JP | 09-176336 | 7/1997 |
| JP | 09-327498 | 12/1997 |
| JP | 10-015033 | 1/1998 |
| JP | 10-024087 | 1/1998 |
| JP | 10-024088 | 1/1998 |
| JP | 10-043272 | 2/1998 |
| JP | 10-071185 | 3/1998 |
| JP | 10-085305 | 4/1998 |
| JP | 10-085306 | 4/1998 |
| JP | 10-108893 | 4/1998 |
| JP | 10-179689 | 7/1998 |
| JP | 10-201819 | 8/1998 |
| JP | 10-201820 | 8/1998 |
| JP | 10-201821 | 8/1998 |
| JP | 10-216200 | 8/1998 |
| JP | 10-218252 | 8/1998 |
| JP | 10-236541 | 9/1998 |
| JP | 10-243990 | 9/1998 |
| JP | 10-277132 | 10/1998 |
| JP | 11-009659 | 1/1999 |
| JP | 11-076367 | 3/1999 |
| JP | 11-079258 | 3/1999 |

| | | | | | | |
|---|---|---|---|---|---|---|
| JP | 11-114016 | 4/1999 | | WO | WO 92/02271 | 2/1992 |
| JP | 11-155930 | 6/1999 | | WO | WO 94/16664 | 8/1994 |
| JP | 11-285518 | 10/1999 | | WO | WO 95/07665 | 3/1995 |
| JP | 2000-005276 | 1/2000 | | WO | WO 95/26117 | 9/1995 |
| JP | 2000-007050 | 1/2000 | | WO | WO 97/37628 | 10/1997 |
| JP | 2000-014746 | 1/2000 | | WO | WO 97/42897 | 11/1997 |
| JP | 2000-187111 | 7/2000 | | WO | WO 98/10733 | 3/1998 |
| JP | 2000-262589 | 9/2000 | | WO | WO 98/34842 | 8/1998 |
| JP | 2000-262591 | 9/2000 | | WO | WO 99/23966 | 5/1999 |
| JP | 2000-316951 | 11/2000 | | WO | WO 99/24086 | 5/1999 |
| JP | 2000-390350 | 11/2000 | | WO | WO 99/27885 | 6/1999 |
| JP | 2001-046470 | 2/2001 | | WO | WO 00/30850 | 6/2000 |
| JP | 2001-097394 | 4/2001 | | WO | WO 00/57935 | 10/2000 |
| JP | 2002-052065 | 2/2002 | | WO | WO 01/08732 | 2/2001 |
| JP | 2002-136570 | 5/2002 | | WO | WO 01/35898 | 5/2001 |
| JP | 2002-160771 | 6/2002 | | WO | WO 01/89478 | 11/2001 |
| JP | 2002-165862 | 6/2002 | | WO | WO 02/01129 | 1/2002 |
| JP | 2002-200140 | 7/2002 | | WO | WO 03/068136 | 8/2003 |
| JP | 2003-054574 | 2/2003 | | WO | WO 03/075982 | 9/2003 |
| JP | 2003-081356 | 3/2003 | | WO | WO 03/082549 | 10/2003 |
| JP | 2003-159308 | 6/2003 | | WO | WO 03/092574 | 11/2003 |
| JP | 2003-205013 | 7/2003 | | | | |
| JP | 2003-246731 | 9/2003 | | | | |
| JP | 2003-284761 | 10/2003 | | | | |
| JP | 2004-059138 | 2/2004 | | | | |
| WO | WO 83/01569 | 5/1983 | | | | |

OTHER PUBLICATIONS

English Translation of JP 2001-097394.
English Translation of JP 2000-390350.
Partial English Translation of EP 1 103 487.

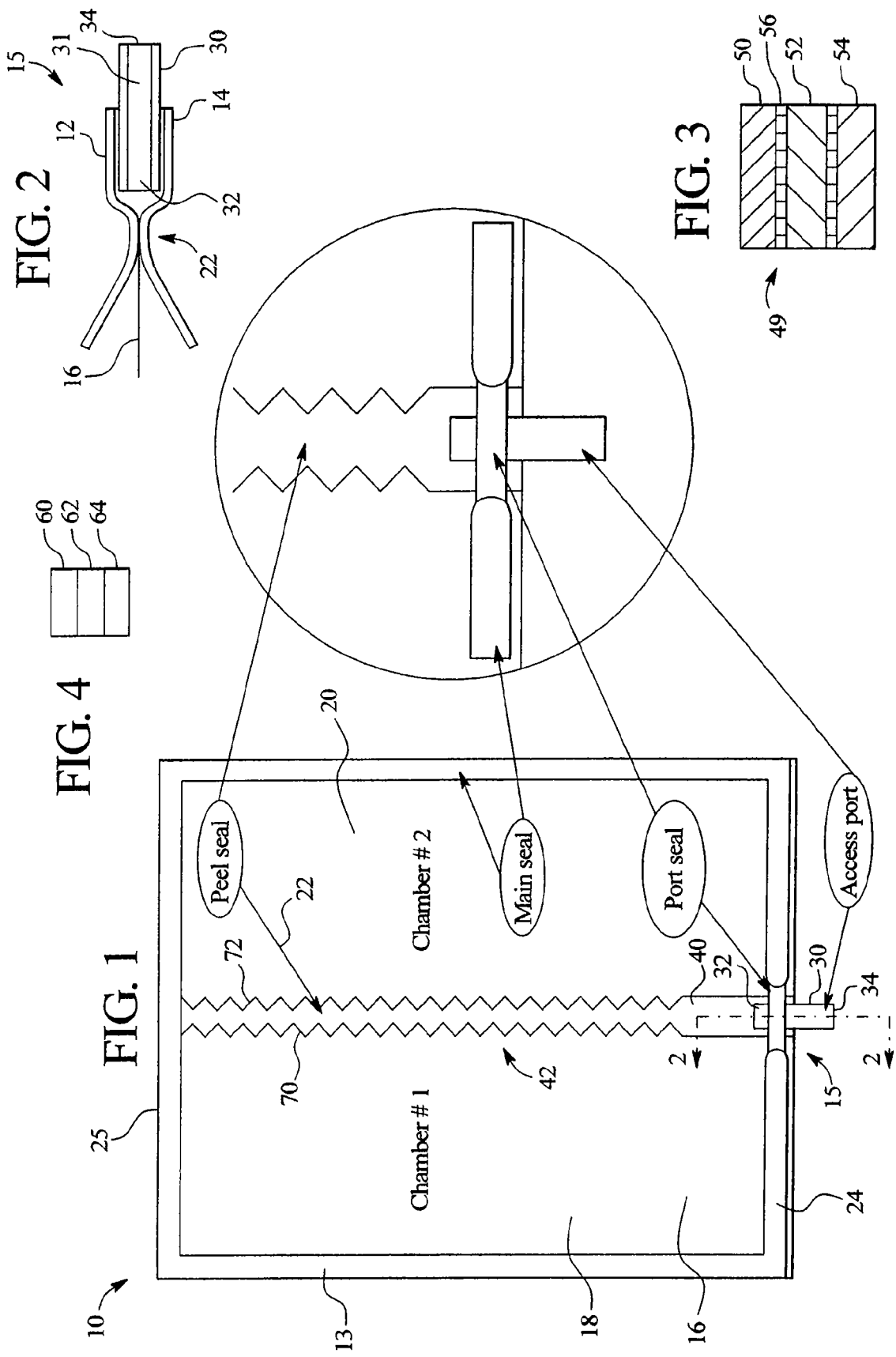

PEELABLE SEAL CLOSURE ASSEMBLY

CROSS-REFERENCE TO RELATED APPLICATIONS

This application is a continuation of U.S. patent application Ser. No. 10/792,021 filed Mar. 3, 2004. This application is also a continuation-in-part application of U.S. patent application Ser. No. 09/439,826 filed on Nov. 12, 1999, the disclosures of each application are incorporated herein by reference.

FEDERALLY SPONSORED RESEARCH OR DEVELOPMENT

Not Applicable.

BACKGROUND OF THE INVENTION

The present invention relates to a container for delivering fluids. In particular, it relates to a fluid access assembly for a flowable materials container wherein a conduit of the assembly has an inlet closed by a peel seal structure. The peel seal is activatable by applying fluid pressure to the peel seal structure. This assembly can be used in flowable materials containers and has been found particularly useful with single chamber and multiple chamber medical solution containers.

Multiple chamber containers having sub-chambers separated by a peel seal, frangible seal or other fluid connecting device are widely used to separately store two or more components that are mixed inside the container prior to administering the mixed solution to a patient. The components can be in a powder or liquid form and are typically mixed together to form a therapeutic solution. Such solutions can include intravenous solutions, nutritional solutions, drug solutions, enteral solutions, parenteral solutions, dialysis solutions, pharmacological agents including gene therapy and chemotherapy agents, and many other fluids that may be administered to a patient.

Due to stability, compatibility, or other concerns, some medical solutions have to be stored separately prior to administration to a patient. These solutions may be stored in separate containers, but are often stored in separate chambers of a single container. The chambers and solutions are often separated by a frangible heat seal. Examples of such containers are disclosed in U.S. Pat. Nos. 5,209,347; 5,176,634; and 4,608,043. These prior art containers have frangible seals to permit the seal to be broken by hand pressure against the sides of the bag to force the contents to break the seal and permit mixing between the components. Peelable seals are among the frangible seals used that permit the seal to be separated by pulling on opposite sides of the container, or by squeezing the container sidewalls.

The chambered container is typically made from a web of flexible polymeric materials. Numerous polymeric films have been developed for use in such containers, and can be a monolayer structure or a multiple layer structure. Containers can also have multiple webs where the webs are joined along peripheral edges and the planar surface of individual webs are not necessarily attached to one another. The monolayer structure can be made from a single polymer, or from a polymer blend. Multiple layer structures can be formed by co-extrusion, extrusion lamination, lamination, or any suitable means. The multiple layer structures can include layers such as a solution contact layer, a scratch resistant layer, a barrier layer for preventing permeation of oxygen or water vapor, tie layers, or other layers. Selection of the appropriate film depends on the solution to be contained within the container.

The container is typically formed by placing one or more polymeric film sheets in registration by their peripheral portions and sealing the outer periphery to form a fluid tight pouch. The peripheral seals are permanent, and therefore, do not peel. The sheets are sealed by heat sealing, radio frequency sealing, thermal transfer welding, adhesive sealing, solvent bonding, ultrasonic or laser welding.

Blown extrusion is another method used to make the pouch. Blown extrusion is a process that provides a moving tube of extrudate exiting an extrusion die. Air under pressure inflates the tube. Longitudinal ends of the tube are sealed to form the pouch.

A peelable seal having a peel strength lower than the peripheral seal can be formed in the container by various methods such as using a lower heat sealing temperature than used to form the peripheral seal. A peelable seal typically has an initial or peak peel force required to initiate separation of the peelable seal, and a plateau force to propagate the separation. Before steam sterilization, these forces are essentially equal. After the chambered container is filled with solution, it is typically steam sterilized at a temperature of 121° C. During steam sterilization, stress is applied to the edges of the peelable seal. When stress is applied to the peelable seal at a temperature above the softening point of the container material during sterilization, deformation occurs at the seal edge. The deformation reduces stress concentrations at the edge of the seal, increasing the peak peel force necessary to initiate peeling of the peelable seal. After steam sterilization, the peak peel force can be significantly greater than the plateau force. This increased peak peel force is detrimental to use of the multichambered container by making it more difficult to initiate peeling to open the container. This is especially true for patients using the medical solutions who may be infirmed or elderly and unable to provide the force necessary to initiate peeling. Moreover, the peak peel force is difficult to control, some containers remaining easy to initiate peeling in the peelable seal, while others becoming almost impossible to initiate by hand.

SUMMARY OF THE INVENTION

Disclosed herein is a flowable materials conveyance assembly having a conduit having a wall defining a first pathway for conveying flowable materials and having an inlet to the pathway and an outlet from the pathway; and a multiple layer structure having a first web and a second web connected together along an interface proximate the inlet, the multiple layer structure is capable of moving from a sealed position to an activated position in response to materials delivered under pressure to the structure along a second pathway different from the first pathway to allow flowable materials to enter the inlet.

Also disclosed herein is a closure assembly for a container having opposing sidewalls defining a chamber therebetween; and a conduit having a portion extending into the chamber and having a fluid inlet, interfacing portions of the sidewalls are connected together along a peel seal over the inlet to define a closure.

Also disclosed herein is a flowable materials container having a pair of opposing sidewalls defining a chamber therebetween, interfacing portions of opposed sidewalls are sealed together along a peel seal to define at least two separate sub-chambers; and a conduit having a portion extending into the chamber and having a fluid inlet, the fluid inlet is closed by a portion of the peel seal.

Also disclosed herein is a method for mixing two components separately stored in sub-chambers of a dual chamber container including the steps of: (1) providing a fluid container having a first chamber, a second chamber a peel seal dividing the first chamber from the second chamber, and a fluid access device having a fluid inlet positioned inside the chamber, the fluid inlet being sealed closed by a first portion of the peel seal; (2) activating a second portion of the peel seal to provide a fluid pathway between the first chamber and the second chamber without activating the first portion; and (3) activating the first portion of the peel seal to open the fluid inlet.

These and other aspects and attributes of the present invention will be discussed with reference to the following drawings and accompanying specification.

BRIEF DESCRIPTION OF THE FIGURES

FIG. 1 is a plan view of a multichambered container including a peelable seal;

FIG. 2 is a cross-sectional view taken along lines 2-2 of FIG. 1;

FIG. 3 is a cross-sectional view of a multiple layer structure;

FIG. 4 is a cross-sectional view of another embodiment of a multiple layer structure;

DETAILED DESCRIPTION OF THE INVENTION

Figure 5:
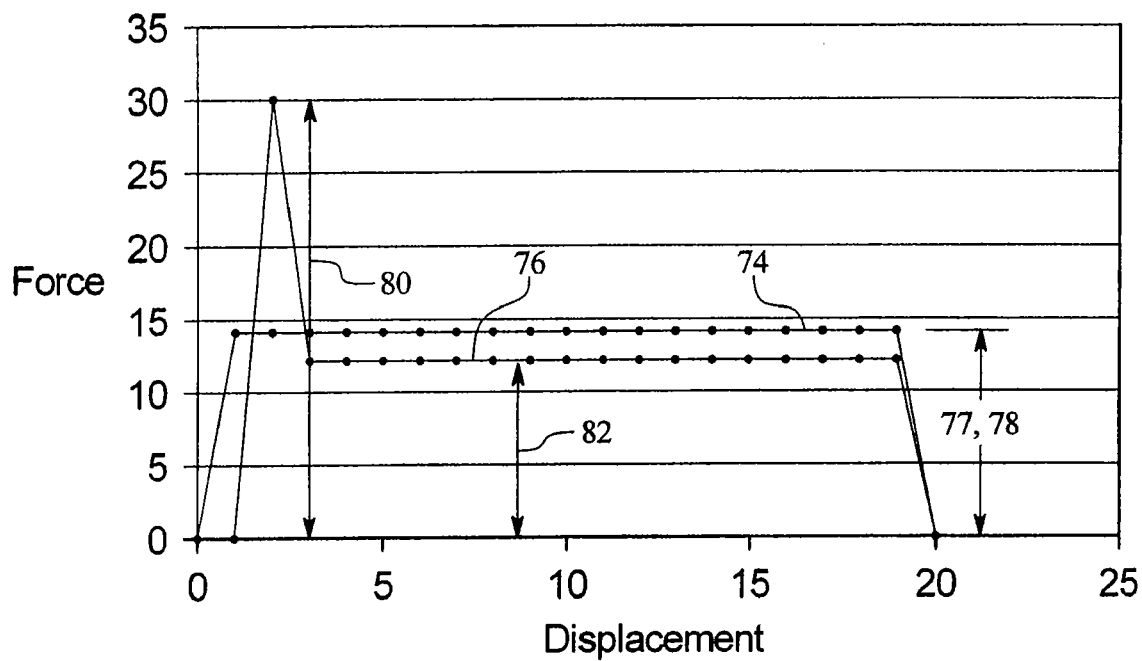
FIG. 5 is a graph showing typical force vs. displacement curves for a peelable seal before and after sterilization.

The present invention is susceptible of embodiments in many different forms. Preferred embodiments of the invention are disclosed with the understanding that the present disclosure is to be considered as exemplifications of the principles of the invention and are not intended to limit the broad aspects of the invention to the embodiments illustrated.

FIGS. 1 and 2 show container 10 having a first sidewall 12 and a second sidewall 14 having a permanent peripheral seal 13 and a closure assembly 15. The container has a chamber 16 that is divided into a first sub-chamber 18 and a second sub-chamber 20 by a peelable seal 22. The seal 22 extends longitudinally of the container from end seam 24 to end seam 25. The seal is effective in separating components such as two liquids, a solid and a liquid, two gasses, a gas and a liquid and a gas and a solid.

As best seen in FIG. 2, the closure assembly 15 has a conduit 30 having a fluid flow path 31, a fluid inlet 32 and a fluid outlet 34. A first portion 40 of the peelable seal 22 extends over the fluid inlet 32 to seal the conduit from fluid flow either inward to the chamber or outward from the chamber. The first portion 40 of the peel sealable seal may sometimes be referred to as a closure or peelable closure. As will be described in greater detail below, the peelable seal 22 has a peelable seal activation force required to move the seal from a closed or sealed position to an open or activated position. The peelable seal 22 is designed to first activate along a second portion 42 of the peelable seal followed by activation of the first portion 40. The second portion 42 is spaced a distance from the first portion 40 to ensure mixing of the components of the first and second sub-chambers 18, 20 before the outlet conduit inlet 32 is open and placed in fluid communication with the mixed contents. In a preferred form of the invention, the second portion 42 is generally centrally disposed along the length and width dimensions of the container.

The closure 40 is capable of blocking fluid traveling in either incoming or outgoing directions through the conduit 30. For single or multiple chamber fluid containers, the peelable seal 22 will block an incoming or outgoing flow of fluid, until the flow of fluid is pressurized above the peel seal activation force. Thus, the peelable seal protects against unwanted ingress or egress of fluids from the container.

The Sidewall Materials and Layer Structures

The container 10 is preferably made principally of flexible polymeric materials, although the container could include non-polymeric materials such as metal foils without departing from the invention. Numerous polymeric films have been developed for use in containers. Suitable films may be of a monolayer structure or a multiple layer structure. The monolayer structure can be made from a single polymer, or from a polymer blend. The multiple layer structures can include layers such as a solution contact layer, a scratch resistant layer, a barrier layer for preventing permeation of oxygen or water vapor, tie layers, or other layers. It is also contemplated to use more than one web of film for one or both sidewalls.

Selection of the appropriate film depends on the solution or solutions to be contained within the container. Appropriate polymeric materials are generally selected from homopolymers and copolymers of polyolefins, polyamides, polyesters, polybutadiene, styrene and hydrocarbon copolymers, polyimides, polyester-polyethers, polyamide-polyethers to name a few.

The seal layer for a multiple chamber container should display bi-modal behavior. What is meant by bi-modal behavior is that the material is capable of forming a permanent seal under one set of sealing or manufacturing conditions and a peelable seal at a second set of sealing or manufacturing conditions. The seal layer can be a homophase polymer, or a matrix-phase polymer system. Suitable homophase polymers include polyolefins and more preferably polypropylene and most preferably a propylene and ethylene copolymer as described in EP 0875231, which is incorporated herein by reference.

It is also possible to have a seal layer having wall 12 and 14 of differing materials that are not compatible with one another. U.S. patent application Ser. No. 10/351,004, which is incorporated herein by reference, discloses that containers made from such incompatible material, in some instances, may not readily form permanent seals. This problem can be overcome by wrapping a section of one sidewall over an outside surface of the opposite sidewall and joined thereto. This method of sealing is disclosed in U.S. Pat. No. 6,024,220 which is incorporated herein by reference and made a part hereof.

Suitable matrix-phase polymer systems will have at least two components. The two components can be blended together or can be produced in a two-stage reactor process. Typically, the two components will have different melting point or glass transition temperatures. In the case where one of the components is amorphous, its glass transition temperature will be lower than the melting point of the other components. Examples of suitable matrix-phase polymer system includes a component of a homopolymer or copolymer of a polyolefin and a second component of a styrene and hydrocarbon copolymer. Another suitable matrix-phase system includes blends of polyolefins such as polypropylene with polyethylene, or polypropylene with a high isotactic index (crystalline) with polypropylene with a lower isotactic index (amorphous), or a polypropylene homopolymer with a propylene and α-olefin copolymer.

Suitable polyolefins include homopolymers and copolymers obtained by polymerizing alpha-olefins containing from 2 to 20 carbon atoms, and more preferably from 2 to 10 carbons. Therefore, suitable polyolefins include polymers and copolymers of propylene, ethylene, butene-1, pentene-1, 4-methyl-1-pentene, hexene-1, heptene-1, octene-1, nonene-1 and decene-1. Most preferably the polyolefin is a homopolymer or copolymer of propylene or a homopolymer or copolymer of polyethylene.

Suitable homopolymers of polypropylene can have a stereochemistry of amorphous, isotactic, syndiotactic, atactic, hemiisotactic or stereoblock. In one preferred form of the invention, the homopolymer of polypropylene is obtained using a single site catalyst.

Suitable copolymers of propylene are obtained by polymerizing a propylene monomer with an α-olefin having from 2 to 20 carbons. In a more preferred form of the invention, the propylene is copolymerized with ethylene in an amount by weight from about 1% to about 20%, more preferably from about 1% to about 10% and most preferably from 2% to about 5% by weight of the copolymer. The propylene and ethylene copolymers may be random or block copolymers. The propylene copolymer may also be obtained using a single site catalyst.

It is also possible to use a blend of polypropylene and α-olefin copolymers wherein the propylene copolymers can vary by the number of carbons in the α-olefin. For example, the present invention contemplates blends of propylene and α-olefin copolymers wherein one copolymer has a 2 carbon α-olefin and another copolymer has a 4 carbon α-olefin. It is also possible to use any combination of α-olefins from 2 to 20 carbons and most preferably from 2 to 8 carbons. Accordingly, the present invention contemplates blends of propylene and α-olefin copolymers wherein a first and second α-olefins have the following combination of carbon numbers: 2 and 6, 2 and 8, 4 and 6, 4 and 8. It is also contemplated using more than 2 polypropylene and α-olefin copolymers in the blend. Suitable polymers can be obtained using a catalloy procedure. Suitable homopolymers of ethylene include those having a density of greater than 0.915 g/cc and includes low density polyethylene (LDPE), medium density polyethylene (MDPE) and high density polyethylene (HDPE).

Suitable copolymers of ethylene are obtained by polymerizing ethylene monomers with an α-olefin having from 3 to 20 carbons, more preferably 3-10 carbons and most preferably from 4 to 8 carbons. It is also desirable for the copolymers of ethylene to have a density as measured by ASTM D-792 of less than about 0.915 g/cc and more preferably less than about 0.910 g/cc and even more preferably less than about 0.900 g/cc. Such polymers are oftentimes referred to as VLDPE (very low density polyethylene) or ULDPE (ultra low density polyethylene). Preferably the ethylene α-olefin copolymers are produced using a single site catalyst and even more preferably a metallocene catalyst systems. Single site catalysts are believed to have a single, sterically and electronically equivalent catalyst position as opposed to the Ziegler-Natta type catalysts which are known to have a mixture of catalysts sites. Such single-site catalyzed ethylene α-olefins are sold by Dow under the trade name AFFINITY, DuPont Dow under the trademark ENGAGE®, Eastman Kodak under the trade name MXSTEN, and by Exxon under the trade name EXACT. These copolymers shall sometimes be referred to herein as m-ULDPE.

Suitable copolymers of ethylene also include ethylene and lower alkyl acrylate copolymers, ethylene and lower alkyl substituted alkyl acrylate copolymers and ethylene vinyl acetate copolymers having a vinyl acetate content of from about 8% to about 40% by weight of the copolymer. The term "lower alkyl acrylates" refers to comonomers having the formula set forth in Diagram 1:

Diagram 1

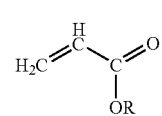

The R group refers to alkyls having from 1 to 17 carbons. Thus, the term "lower alkyl acrylates" includes but is not limited to methyl acrylate, ethyl acrylate, butyl acrylate and the like.

The term "alkyl substituted alkyl acrylates" refers to comonomers having the formula set forth in Diagram 2:

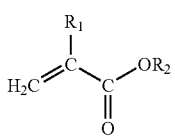

Diagram 2

$R_1$ and $R_2$ are alkyls having 1-17 carbons and can have the same number of carbons or have a different number of carbons. Thus, the term "alkyl substituted alkyl acrylates" includes but is not limited to methyl methacrylate, ethyl methacrylate, methyl ethacrylate, ethyl ethacrylate, butyl methacrylate, butyl ethacrylate and the like.

Suitable polybutadienes include the 1,2- and 1,4-addition products of 1,3-butadiene (these shall collectively be referred to as polybutadienes). In a more preferred form of the invention, the polymer is a 1,2-addition product of 1,3 butadiene (these shall be referred to as 1,2 polybutadienes). In an even more preferred form of the invention, the polymer of interest is a syndiotactic 1,2-polybutadiene and even more preferably a low crystallinity, syndiotactic 1,2 polybutadiene. In a preferred form of the invention, the low crystallinity, syndiotactic 1,2 polybutadiene will have a crystallinity less than 50%, more preferably less than about 45%, even more preferably less than about 40%, even more preferably the crystallinity will be from about 13% to about 40%, and most preferably from about 15% to about 30%. In a preferred form of the invention, the low crystallinity, syndiotactic 1,2 polybutadiene will have a melting point temperature measured in accordance with ASTM D 3418 from about 70° C. to about 120° C. Suitable resins include those sold by JSR (Japan Synthetic Rubber) under the grade designations: JSR RB 810, JSR RB 820, and JSR RB 830.

Suitable polyesters include polycondensation products of di-or polycarboxylic acids and di or poly hydroxy alcohols or alkylene oxides. In a preferred form of the invention, the polyester is a polyester ether. Suitable polyester ethers are obtained from reacting 1,4 cyclohexane dimethanol, 1,4 cyclohexane dicarboxylic acid and polytetramethylene glycol ether and shall be referred to generally as PCCE. Suitable PCCE's are sold by Eastman under the trade name ECDEL. Suitable polyesters further include polyester elastomers which are block copolymers of a hard crystalline segment of polybutylene terephthalate and a second segment of a soft (amorphous) polyether glycols. Such polyester elastomers are sold by DuPont Chemical Company under the trade name HYTREL®.

Suitable polyamides include those that result from a ring-opening reaction of lactams having from 4-12 carbons. This group of polyamides therefore includes nylon 6, nylon 10 and nylon 12. Acceptable polyamides also include aliphatic polyamides resulting from the condensation reaction of di-amines having a carbon number within a range of 2-13, aliphatic polyamides resulting from a condensation reaction of di-acids having a carbon number within a range of 2-13, polyamides resulting from the condensation reaction of dimer fatty acids, and amide containing copolymers. Thus, suitable aliphatic polyamides include, for example, nylon 6,6, nylon 6,10 and dimer fatty acid polyamides.

Suitable styrene and hydrocarbon copolymers include styrene and the various substituted styrenes including alkyl substituted styrene and halogen substituted styrene. The alkyl group can contain from 1 to about 6 carbon atoms. Specific examples of substituted styrenes include alpha-methylstyrene, beta-methylstyrene, vinyltoluene, 3-methylstyrene, 4-methylstyrene, 4-isopropylstyrene, 2,4-dimethylstyrene, o-chlorostyrene, p-chlorostyrene, o-bromostyrene, 2-chloro-4-methylstyrene, etc. Styrene is the most preferred.

The hydrocarbon portion of the styrene and hydrocarbon copolymer includes conjugated dienes. Conjugated dienes which may be utilized are those containing from 4 to about 10 carbon atoms and more generally, from 4 to 6 carbon atoms. Examples include 1,3-butadiene, 2-methyl-1,3-butadiene (isoprene), 2,3-dimethyl-1,3-butadiene, chloroprene, 1,3-pentadiene, 1,3-hexadiene, etc. Mixtures of these conjugated dienes also may be used such as mixtures of butadiene and isoprene. The preferred conjugated dienes are isoprene and 1,3-butadiene.

The styrene and hydrocarbon copolymers can be block copolymers including di-block, tri-block, multi-block, star block and mixtures of the same. Specific examples of diblock copolymers include styrene-butadiene, styrene-isoprene, and the hydrogenated derivatives thereof. Examples of triblock polymers include styrene-butadiene-styrene, styrene-isoprene-styrene, alpha-methylstyrene-butadiene-alpha-methylstyrene, and alpha-methylstyrene-isoprene-alpha-methylstyrene and hydrogenated derivatives thereof.

The selective hydrogenation of the above block copolymers may be carried out by a variety of well known processes including hydrogenation in the presence of such catalysts as Raney nickel, noble metals such as platinum, palladium, etc., and soluble transition metal catalysts. Suitable hydrogenation processes which can be used are those wherein the diene-containing polymer or copolymer is dissolved in an inert hydrocarbon diluent such as cyclohexane and hydrogenated by reaction with hydrogen in the presence of a soluble hydrogenation catalyst. Such procedures are described in U.S. Pat. Nos. 3,113,986 and 4,226,952, the disclosures of which are incorporated herein by reference and made a part hereof.

Particularly useful hydrogenated block copolymers are the hydrogenated block copolymers of styrene-isoprene-styrene, such as a styrene-(ethylene/propylene)-styrene block polymer. When a polystyrene-polybutadiene-polystyrene block copolymer is hydrogenated, the resulting product resembles a regular copolymer block of ethylene and 1-butene (EB). As noted above, when the conjugated diene employed is isoprene, the resulting hydrogenated product resembles a regular copolymer block of ethylene and propylene (EP). One example of a commercially available selectively hydrogenated copolymer is KRATON G-1652 which is a hydrogenated SBS triblock comprising 30% styrene end blocks and a midblock equivalent is a copolymer of ethylene and 1-butene (EB). This hydrogenated block copolymer is often referred to as SEBS. Other suitable SEBS or SIS copolymers are sold by Kurrarry under the tradename SEPTON® and HYBRAR®. It may also be desirable to use graft modified styrene and hydrocarbon block copolymers by grafting an alpha,beta-unsaturated monocarboxylic or dicarboxylic acid reagent onto the selectively hydrogenated block copolymers described above.

The block copolymers of the conjugated diene and the vinyl aromatic compound are grafted with an alpha, beta-unsaturated monocarboxylic or dicarboxylic acid reagent. The carboxylic acid reagents include carboxylic acids per se and their functional derivatives such as anhydrides, imides, metal salts, esters, etc., which are capable of being grafted onto the selectively hydrogenated block copolymer. The grafted polymer will usually contain from about 0.1 to about 20%, and preferably from about 0.1 to about 10% by weight based on the total weight of the block copolymer and the carboxylic acid reagent of the grafted carboxylic acid. Specific examples of useful monobasic carboxylic acids include acrylic acid, methacrylic acid, cinnamic acid, crotonic acid, acrylic anhydride, sodium acrylate, calcium acrylate and magnesium acrylate, etc. Examples of dicarboxylic acids and useful derivatives thereof include maleic acid, maleic anhydride, fumaric acid, mesaconic acid, itaconic acid, citraconic acid, itaconic anhydride, citraconic anhydride, monomethyl maleate, monosodium maleate, etc. The styrene and hydrocarbon block copolymer can be modified with an oil such as the oil modified SEBS sold by the Shell Chemical Company under the product designation KRATON G2705.

FIG. 3 shows a multiple layer film 49 having a seal layer 50 an intermediate layer 52 and an external layer 54. Tie layers 56 may be employed to attach the seal layer 50 to the intermediate layer 52 and to attach the intermediate layer 52 to the external layer 54. In a preferred form of the invention the seal layer is a blend of polypropylene, an ethylene α-olefin copolymer and a styrene and hydrocarbon copolymer. In a more preferred form of the invention, the polypropylene is a polypropylene ethylene copolymer, the ethylene α-olefin copolymer is a LLDPE having a density of less than 0.915 g/cc and the styrene and hydrocarbon copolymer is a block copolymer and preferably a tri-block copolymer of styrene-ethylene-butylene-styrene or a blend of an SEBS triblock with an SEBS diblock as a minor component. The relative proportions of the components are preferably from about 55% to 75% of the PP by weight, from 5% to 20% by weight of the LLDPE, and from 10% to 20% by weight of the SEBS. The ternary blend of the seal layer is capable of forming a permanent seal and a peel seal at a temperature of from about 123 to 128° C. A permanent seal is achieved at sealing temperatures above 160° C.

The intermediate layer 52 may be selected from any of the polyamides set forth herein and most preferably is a blend of from about 85 to 98% polyamide 6 and from 2 to 15% polyamide 616T.

The external layer 54 is selected from polypropylene polymer, and most preferably is a propylene ethylene copolymer with an ethylene content of less than 6% by weight of the copolymer.

The details of the film 49 are more fully set out in U.S. patent application Ser. No. 09/439,826, filed Nov. 12, 1999, which is incorporated in its entirety herein by reference and made a part hereof.

Another suitable film is shown in FIG. 4 having three layers, external layer 60, intermediate layer 62 and seal layer 64. The external layer is a reactor made polypropylene composition having a first component and a second component. The first component is a polypropylene homopolymer and is present in an amount by weight of the composition of 40%. The second component is an ethylene-propylene rubber (ethylene 20% and propylene 80%) and is present in an amount by weight of the composition of 60%. Suitable products for the external layer are sold by Mitsubishi Chemical Company under the trade name Zelas 7023. Zelas 7023 is the subject of U.S. Patent Application Publication No. 2001/0034416 A1 which is incorporated herein by reference in its entirety and made a part hereof.

The intermediate layer 62 is a polymer blend of Zelas 7023 70% by weight and 30% by weight of a random copolymer of styrene and butadiene that has been hydrogenated. Suitable random copolymers of styrene and butadiene are sold by JSR under the trade name Dynaron 2320 P.

The external layer 64 is a polymer blend of 60% by weight Zelas 7023 and 40% by weight of a random copolymer of propylene and ethylene such as the copolymer sold under the trade name Novatec EG 7C.

The film of FIG. 4 displays bi-modal behavior with peel seals being formed at sealing temperatures of about 125° C. and permanent seals are obtained at about 160° C.

Other suitable films for this application include those disclosed in U.S. Pat. Nos. 5,849,843; 5,998,019; 6,083,587; 6,297,046; 5,139,831; 5,577,369; and U.S. Application No. 2003/0077466 A1 which are incorporated herein in their entirety by reference and made a part hereof.

The container 10 is typically formed by placing one or more polymeric film sheets forming the first sidewall 12 and second sidewall 14 in registration by their peripheral portions and sealing their periphery 13 to form a fluid tight pouch. The sheets are typically sealed by heat sealing, radio frequency sealing, thermal transfer welding, adhesive sealing, solvent bonding, and ultrasonic or laser welding. Blown extrusion is another method that may be used to make the pouch. Blown extrusion is a process that provides a moving tube of extrudate exiting an extrusion die. Air under pressure inflates the tube. Longitudinal ends of the tube are sealed to form the pouch. Blown extrusion only requires seals along two peripheral surfaces, where the single or multiple sheet registration method requires seals along one, three, or four peripheral surfaces to form the pouch.

Peelable Seal

The peelable seal 22 is preferably created by heat sealing, but may be made by any of the above-mentioned sealing or welding methods, or any other suitable method. The peelable seal 22 is peelable such that it may be peeled by hand pressure to separate the first sidewall 12 and second sidewall 14 to allow fluid communication between the first chamber 18 and second chamber 20, thereby mixing the components contained in them. The peelable seal 22 is peeled, for example, by gripping the first sidewall 12 and second sidewall 14 of the container 10, and pulling them apart, or be squeezing or pressing the first sidewall 12 and second sidewall 14 to force the fluid in chambers 18 and 20 against the peelable seal 22 with sufficient force to separate the peelable seal 22. The peelable seal 22 is strong enough to withstand external stresses without peeling resulting from ordinary squeezing during handling, shipment, or from accidental dropping.

In a preferred form of the invention, the peel seal will have a peel seal activation force that falls within a range of from about 3 N/15 mm to about 30 N/15 mm. The peel seal can have varying peel seal activation forces across it length. In a preferred form of the invention, the peel seal activation force of the first portion 40 of the peel seal will be greater than the second portion 42. This will promote activation of the second portion of the peel seal before the first portion to ensure mixing of any components in the chambers before the closure is opened to allow fluid flow through the inlet 32. In a preferred form of the invention, the peel seal activation force of the first portion 40 of the peel seal 22 is from about 1 N/15 mm to about 5 N/15 mm higher than the peel seal activation force of the second portion 42 of the peel seal 22.

It is desirable for the peel seal 22 to be capable of adhesive release as opposed to cohesive release. Adhesive release of the peel seal means that the first sidewall 12 separates from the second sidewall 14 without removing any significant portion of one wall with the other. The release generates a minimum of particles to prevent or minimize contamination of the components of the chamber 16 with residual plastic particles.

Figure 13:
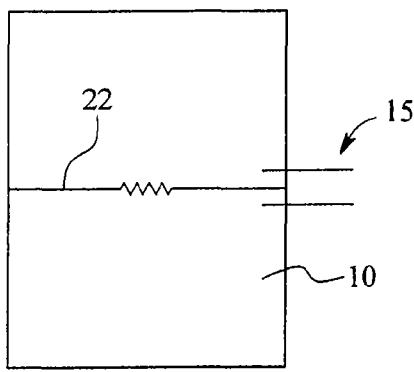
FIG. 13 is a schematic plan view of a peelable seal.
Figure 14:
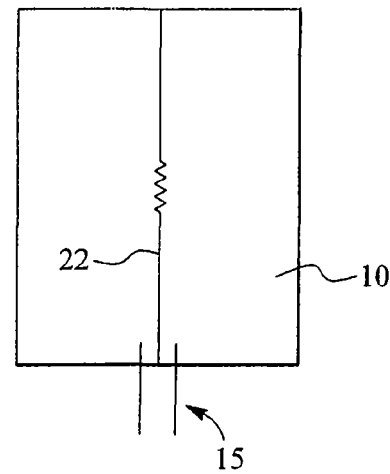
FIG. 14 is a schematic plan view of a peelable seal.
Figure 15:
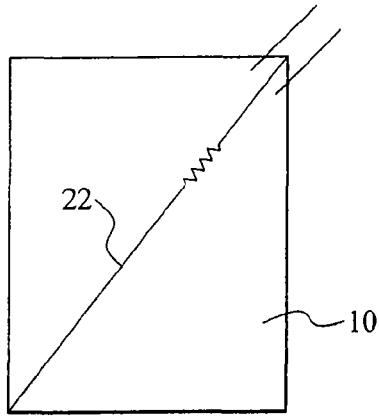
FIG. 15 is a schematic plan view of a peelable seal.
Figure 16:
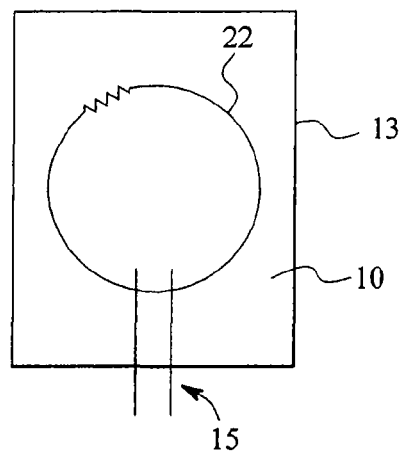
FIG. 16 is a schematic plan view of a peelable seal.
Figure 17:
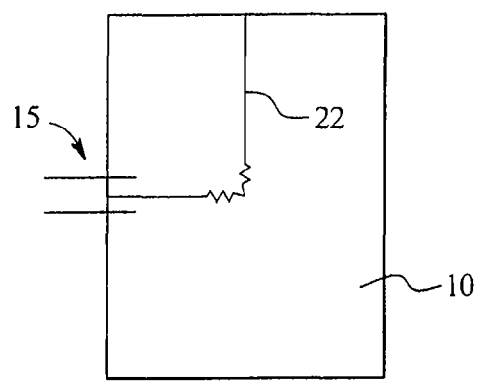
FIG. 17 is a schematic plan view of a peelable seal.

The peelable seal 22 has edges 70 and 72. The peelable seal 22 is shown in FIGS. 1 and 14 as extending along the length dimension of the container, but could also extend between lateral edges as shown in FIG. 13. Alternatively, the peelable seal 22 may be contained completely within the first sidewall 12 and second sidewall 14, and not intersect any part of the peripheral seal 13 (FIG. 16). It is further contemplated that the peelable seal 22 can extend from a corner, a lateral edge, or a longitudinal edge, and terminate elsewhere in the container 10 (FIGS. 15 and 17). The peelable seal 22 may be located anywhere between the first sidewall 12 and second sidewall 14 depending on the relative sizes of the chambers 18 and 20 desired. The chambers 18 and 20 may be filled with medical or other components for forming therapeutic solutions, including intravenous solutions, nutritional solutions, drug solutions, enteral solutions, parenteral solutions, dialysis solutions, pharmacological agents including gene therapy and chemotherapy agents, and many other fluids that may be administered to a patient. The components may be liquid, powder, lyophilized tablet, or other suitable form. The components are introduced into the container 10 and chambers 18 and 20 using any conventional means, such as delivering through a dedicated access port for each chamber 18 and 20. The edges 70 and 72 of the peelable seal 22 abut the fluid in chambers 18 and 20.

Containers are often filled at pressures of up to 60 pounds per square inch (psi). After being filled with solution, the container 10 is typically sterilized using steam. The sterilization typically occurs at a temperature of 121° C.

FIG. 5 shows typical force vs. displacement graph for a peelable seal 22 having straight edges 70 and 72. The x axis of FIG. 5 shows displacement along the length of the peelable seal 22. The y axis shows force necessary to peel the peelable seal 22 at specific points along its length. Curve 74 is the force vs. displacement curve before steam sterilization. Curve 76 is the force vs. displacement curve after steam sterilization. As can be seen from curve 74 of FIG. 5, a force 77 is necessary to initiate peeling the peelable seal 22 prior to steam sterilization. This force 77 is the same as a plateau force 78, which is necessary to propagate peeling after initiation.

As curve 76 shows, after steam sterilization, a peak peel force 80 is required to initiate peeling the peelable seal 22. The peak peel force 80 is significantly greater than a plateau force 82 necessary to propagate peeling. The peak peel force 80 occurs due to sterilization. Sterilization can cause boiling of the solution in the chambers 18 and 20 of the container 10. Boiling can cause expansion of the fluids in the chambers 18 and 20, and thereby further stresses the first sidewall and second sidewall 12 and 14 by forcing them apart. When stress is applied to the peelable seal 22 at a temperature above the softening point of the container material, deformation at the seal edges 70 and 72 occurs. Deformation can also occur because of water expansion and/or shrinkage of the container material due to crystallization, or in the case of stretched container films, stress relaxation. This deformation reduces stress concentration at the seal edges 70 and 72, thereby increasing the force necessary to break the peelable seal 22 to initiate the peeling process. This peak peel force 80 is detrimental to ease of use. Moreover, because of the variable nature of the causes, the peak peel force 80 is variable and hard to control. Some seals 22 may be too easy to activate, peeling during shipping, ordinary handling, or by dropping. Other seals 22 may become almost impossible to initiate peeling by hand.

The present invention overcomes these problems by reducing the peak peel 80 force necessary to initiate peeling at the seal edges 70 and 72. It has been found that changing the shape of the seal edges 70 or 72 from a straight edge on at least the portion of the peelable seal 22 where peeling is to be initiated accomplishes this. This reduces the length of the peelable seal 22 that is subject to stress during exposure to high temperatures during steam sterilization. Thus, the peak peel force 80 occurs only on limited portions of the peelable seal 22.

Figure 6:
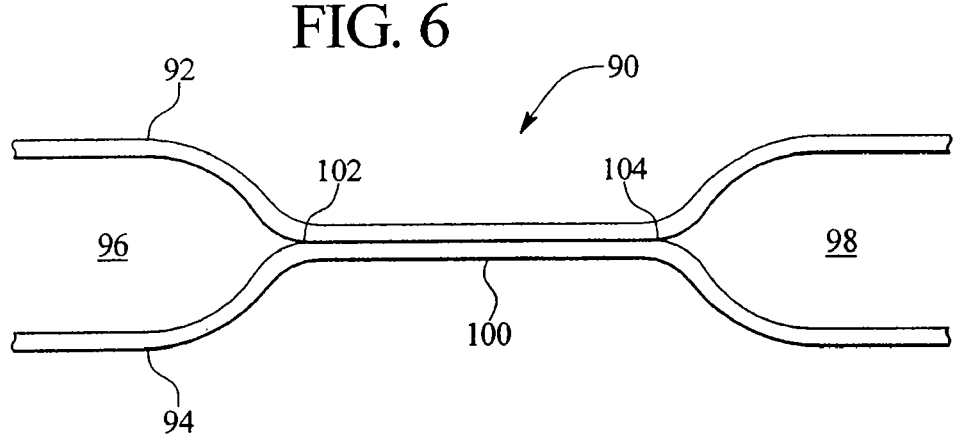
FIG. 6 is a cross-sectional view of a peelable seal having a serrated edge.

FIG. 6 shows a cross-sectional view of a peelable seal 90 in accord with an embodiment of the present invention prior to steam sterilization. First sidewall 92 and second sidewall 94 of a container are sealed at the seal 90. The seal 90 defines chambers 96 and 98 in the container.

Figure 7:
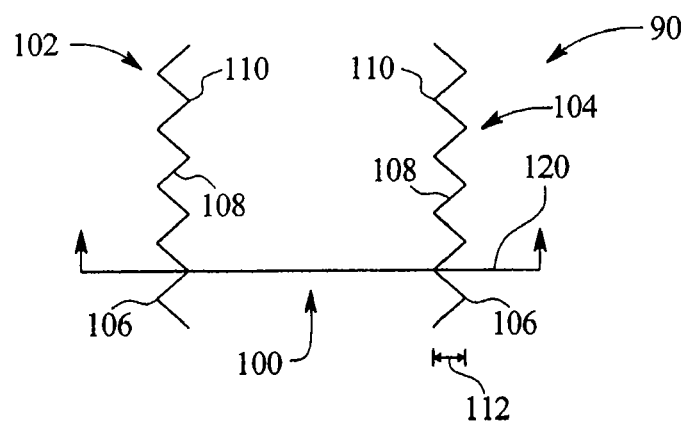
FIG. 7 is an enlarged top view of a peelable seal.
Figure 18:
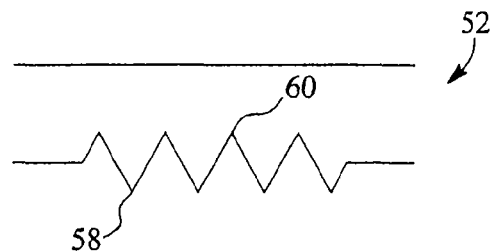
FIG. 18 is a schematic top view of a peelable seal.
Figure 19:
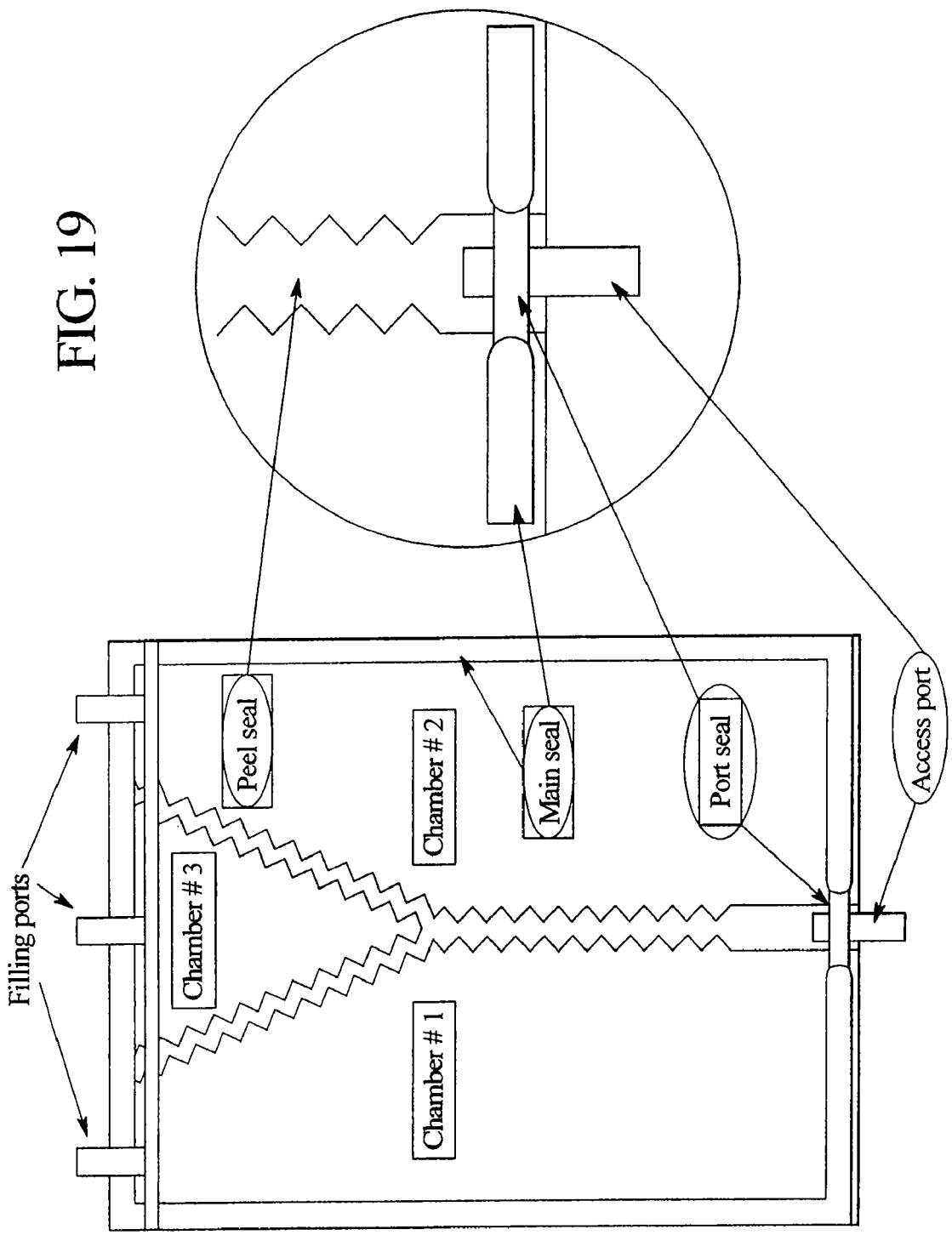
FIG. 19 is a schematic view of a three-chamber container with peel seals separating the chamber, and an administration port, one end of which is embedded in the peel seal.

FIG. 7 is an enlarged top view of the seal 90 of FIG. 6 before steam sterilization. The seal 90 has a sealed area 100, a first seal edge 102, and a second seal edge 104. The first seal edge 102 and second seal edge 104 are serrated, having outer points 106 and angular legs 108 extending at angles from and between the outer points 106. The legs 108 intersect at inner points 110 thereby connecting with outer points 106. Between the inner points 110 and outer points 106 is a depth 112. Though FIG. 7 shows both first seal edge 102 and second seal edge 104 serrated, it is contemplated that only one or the other of the first seal edge 102 or second seal edge 104 may be serrated in accord with the present invention (FIG. 18). It also is contemplated that the serrations can occur over the entire length of the seal 90 or only on selected sections. It is preferred that the serrations be spaced from the peripheral seal 13 of the container 10 to permit peeling of the permanent seal 13.

Figure 8:
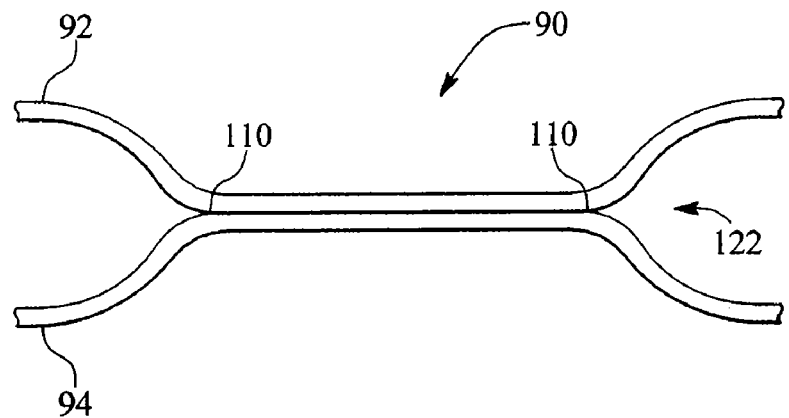
FIG. 8 is a cross-sectional view of a peelable seal.

FIG. 8 shows a cross-sectional view of the seal 90 after steam sterilization taken along line 120 of FIG. 7 intersecting inner points 110. As shown in FIG. 8, an angular joint 122 between the first sidewall 92 and second sidewall 94 occurs at the inner points 110, and is maintained after steam sterilization.

Figure 9:
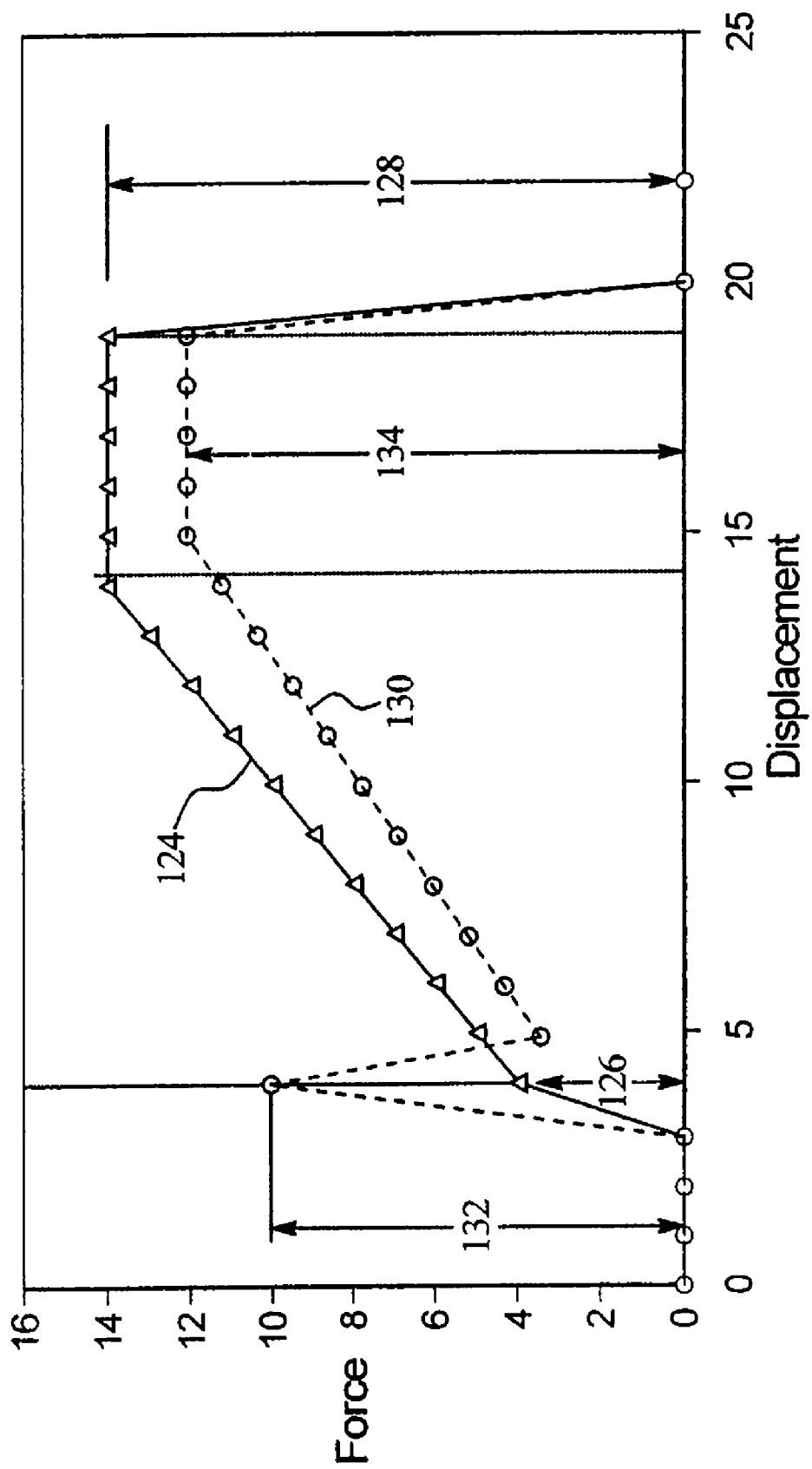
FIG. 9 is a force vs. displacement graph for a peelable seal.

FIG. 9 is a force vs. displacement graph for the serrated peel seal 90 of an embodiment of the present invention. The x axis shows displacement along the length of the seal 90. The y axis shows the force required to peel the seal 90 at points along the length of the seal 90. Curve 124 is the force vs. displacement curve before steam sterilization. An initiation force 126 is necessary to initiate propagation. This force increases essentially linearly to a maximum plateau force 128 to propagate the peeling.

FIG. 9 also shows a curve 130 showing force vs. displacement for the serrated peel seal 90 after steam sterilization. Curve 130 demonstrates the peak peel force 132. The peak peel force 132 is greater than the initiation force 126 before sterilization, however, it is less than a maximum propagation force 134 necessary to continue the peeling process. This results in a greater ease of use of the container because less force is required initiate the peeling process than with a seal with straight seal edges.

During sterilization, only the outer points 106 (FIG. 7) are subject to stress and deformation, and not the inner points 110 or angular legs 108. The outer points 106 are subject to stress because the film tension is at a maximum at the outer points 106. Thus, the stress concentrations present when the seal 90 is made is reduced only at the outer points 106, and not at the angular legs 108 or the inner points 110. Stress concentration is, therefore, retained at inner points 110.

The outer points 106 define an outer stress bearing zone of the peelable seal 90. The outer points 106 bear the stress caused by steam sterilization. The inner points 110 and angular legs 108 define an inner non-stress bearing zone of the seal 90. Creation of a stress-bearing zone may also be accomplished using other shaped seal edges, such as a scalloped seal edge (FIGS. 20 and 22) or a trapezoidal seal edge (FIG. 21), other polygonal or geometric shape.

Figure 20:
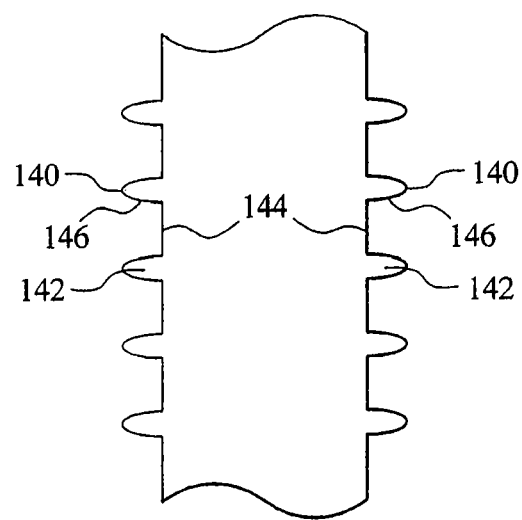
FIG. 20 is a schematic view of a peelable seal.
Figure 21:
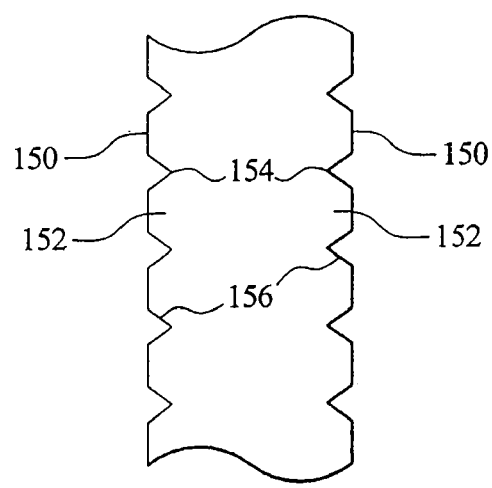
FIG. 21 is a schematic view of a peelable seal.
Figure 22:
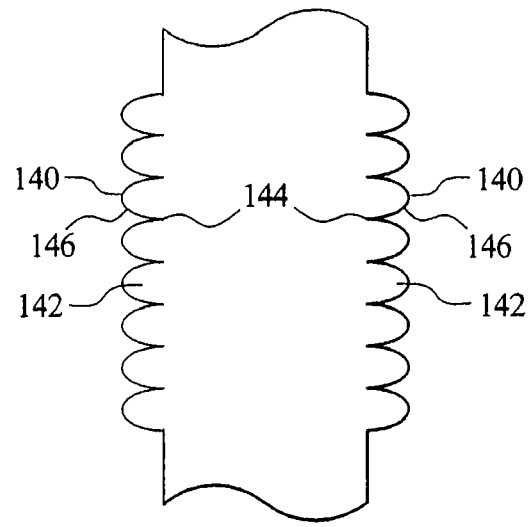
FIG. 22 is a schematic view of a peelable seal.

The stress bearing zone in FIGS. 20 and 22 are the crests 140 of the scallops 142. The non-stress bearing zone includes the troughs 144 and sloping sides 146 of the scallops 142. The stress-bearing zone in FIG. 21 is created by the flat portions 150 of the trapezoids 152. The non-stress bearing zone includes the inner points 154 and sides 156 of the trapezoids 152. The present invention also contemplates other seal edge shapes that create stress bearing zone and a non-stress bearing zone.

In the serrated seal embodiment of FIGS. 6 and 7, the first sidewall 12 and second sidewall 14 of the container are separated first at the inner points 110. The angular joint at inner points 110 further facilitate separation of the first sidewall 12 and second sidewall 14. As a result (FIG. 9), the peak peel force 132 is lower than plateau force 134 for propagating the seal 90, which is the sum of the individual forces required to break the seal 90 at inner points 110, angular legs 108 and outer points 106. Because the outer points 106 are a small length compared to the overall length of the seal 90, the contribution of the points 106 is small when compared to that contributed by the inner points 110 and legs 108. Hence, the plateau force 134 is reduced compared to a peelable seal 90 having straight edges 70 and 72. This allows for providing varying strengths along the length of the peel seal. Peel seal activation forces are reduced in the areas of the serrations which allow for activating the second portion 42 of the peel seal before the first portion 40 (FIG. 1). It also improves the reproducibility of the peak peel force 132. Yet the seal 90 is strong enough to protect the seal 90 against peeling during normal handling. Likewise for scalloped (FIGS. 20 and 22) and trapezoidal (FIG. 21) seal edges, the sidewalls of the container are initially separated at the non-stress bearing zone such that the peak peel force is lower than the plateau force.

For the serrated seal edge embodiment of FIG. 7, an important factor in reducing the peak peel force 132 is the depth 112 of the serrations. The depth 112 controls the slope of the peel force curve 130 before reaching the plateau value 134. The depth 112 must be sufficiently great to permit separation between the peak peel force 132 and the plateau force 134. The minimum depth for reducing the peak peel force 132 is highly dependent on plateau seal force 134 values, i.e., for lower peak peel forces, a greater depth 112 is necessary. Other factors include, mechanical properties of the materials making the container 10, filling volume, filling pressure, and stress occurring during the sterilization process. The greater the volume, the higher the initiation force, and the higher the filling pressure, the higher the initiation force. The number of serrations per unit length is a factor in determining the reduction of the peak peel force 132. The greater the number of serrations, the greater the peak peal force 132. A balance must be struck between peeling force and ability of the seal to withstand normal handling. Experiments have indicated that symmetrical serrations angled at 90°, outer points 106 spaced 8 mm apart, and a depth 112 of 4 mm achieve an acceptable peak peel force 132. Similarly, for embodiments such as the scalloped (FIGS. 20 and 22) or trapezoidal shaped (FIG. 21) seal edges, the depth between the stress-bearing zone and the non-stress-bearing zone must be controlled to balance peeling force and normal handling.

Figure 10:
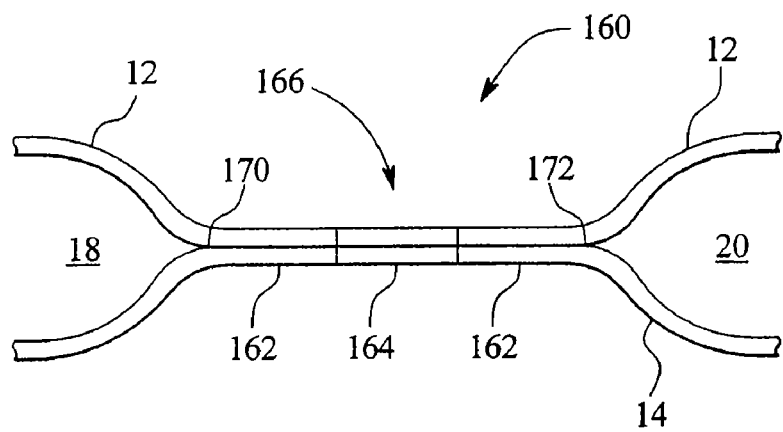
FIG. 10 is a cross-sectional view of a peelable seal.

In another embodiment, the present invention includes a seal 160. FIG. 10 shows a cross-sectional view of the seal 160 before steam sterilization. The seal 160 includes a first seal 162 and a second seal 164. The second seal 164 is preferably located at a central portion 166 of the first seal 162. The seal 160 separates chambers 18 and 20 of the container 10. The first seal 162 also has a lower peel force than the second seal 164. Preferably, the first seal separation force is on the order of 5 N/15 mm, while the second seal separation force is on the order of 15 N/15 mm. The seal 160 is created preferably by heat sealing the first sidewall and second sidewall 12 and 14, and by varying the temperature along the seal 160, such that the temperature to create seal 164 is greater than that for the first seal 162. This causes the first sidewall and second sidewall 12 and 14 at the second seal 164 to adhere together more at the second seal 164 than the first seal 162. In turn, this requires a greater force to separate the first sidewall and second sidewall 12 and 14 at the second seal 164 than the first seal 162. The first seal 162 has a first edge 170 and a second edge 172 that are each in contact with fluid in chambers 18 and 20.

Figure 11:
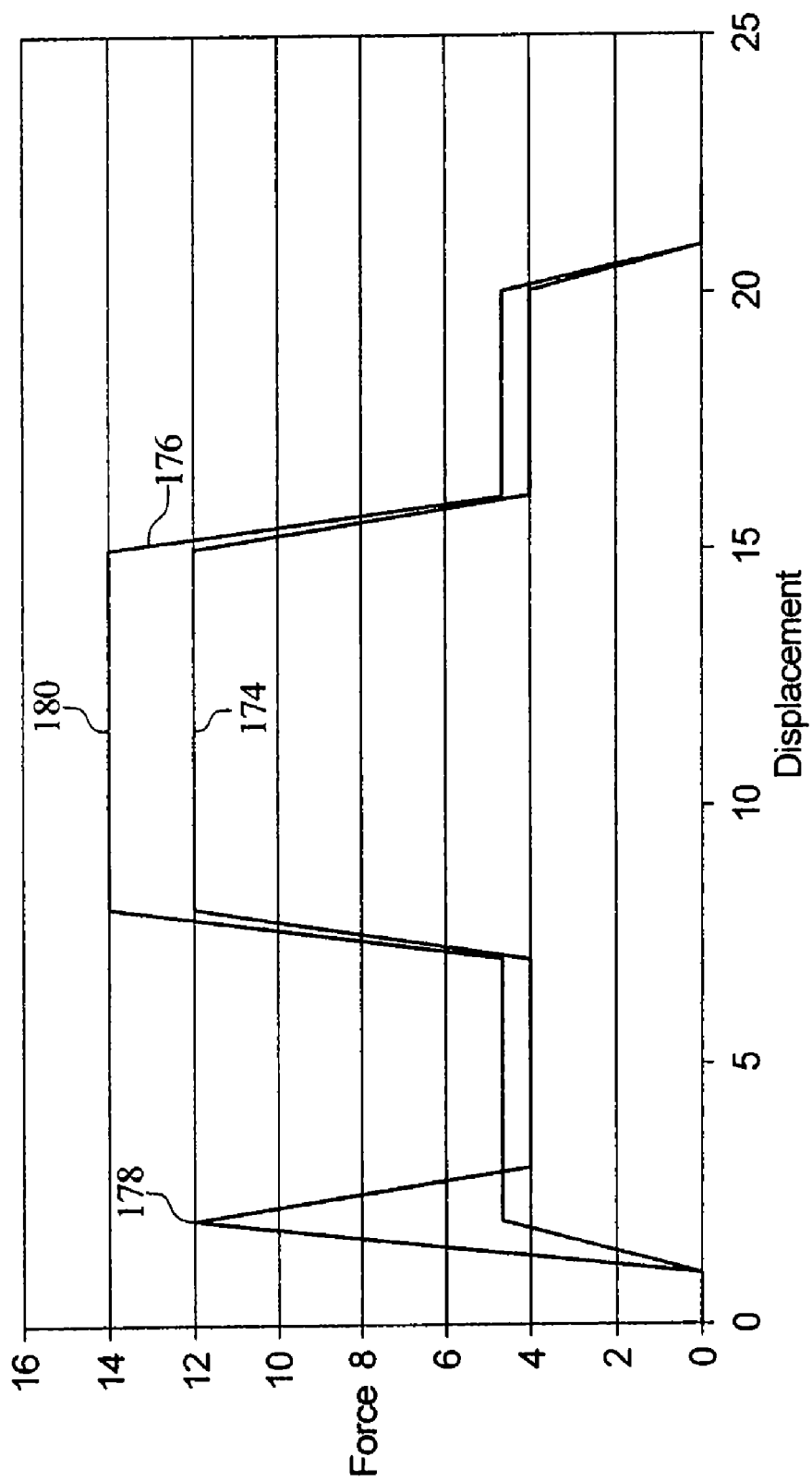
FIG. 11 is force vs. displacement graph for the seal of FIG. 10.

FIG. 11 shows a force vs. displacement graph for the seal 160. Curve 174 shows force vs. displacement before steam sterilization. Curve 176 shows force vs. displacement after steam sterilization. As FIG. 11 demonstrates, the initial peak force 178 of first seal 162 after steam sterilization remains lower than maximum plateau force 180 of the second seal 164.

When sterilized, deformation will occur at the first and second edges 170 and 172. This will increase the peel force at first and second edges 170 and 172 of the first seal 162. Thus, even if a peak peel force at first and second edges 170 and 172 appears as high as three times the plateau value of the first seal 162, it will remain below the peel seal force required to separate the second seal 164 in the central portion. Thus, no peak peel force will occur in the second seal 164. The seal 160 is created by heat sealing the second seal 164 at a higher temperature than the first seal 162.

Figure 12:
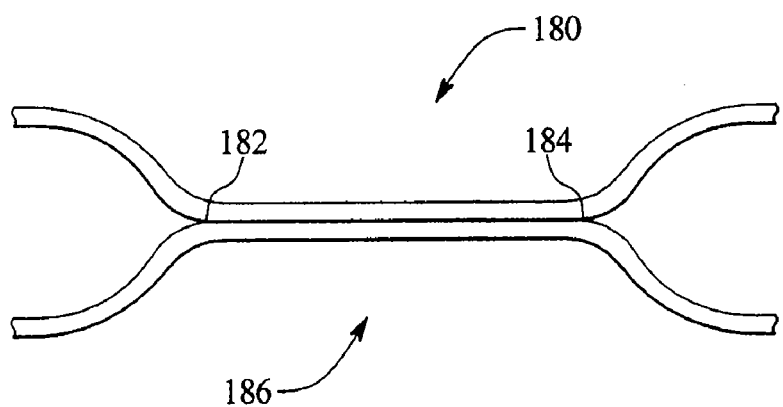
FIG. 12 is a cross-sectional view of a peelable seal.

On a similar principle, an another embodiment shown in FIG. 12, a seal 180 has a peeling force gradient along the width of the seal 180. The seal 180 has first and second edges 182 and 184, and a central portion 186 between the first and second edges 182 and 184. The peel force at the first and second edges 182 and 184 is less, preferably approximately three times less, than the peel force at the central portion 186. As with seal 160 described above, the seal 180 is created by a heat seal having a temperature gradient across its width, greater in the middle and less at the edges. A gradient can be obtained, for instance, by a die having heating elements separated by an insulating material layer, and where the temperature of the central heating element is greater than at the edges. Thus, when a peak peal force occurs at the edges 182 and 184, it remains below the peel force at the central portion 186. The peel force at the edges 182 and 184 preferably being approximately 5 N/15 mm and at the central portion 186 being approximately 15 N/15 mm. In this manner, even if the edges 182 and 184 of the seal 180 experience a peel force increase of three times, it is still the same or less than that in the central portion 186. Thus, no peak peal force occurs.

Figure 23:
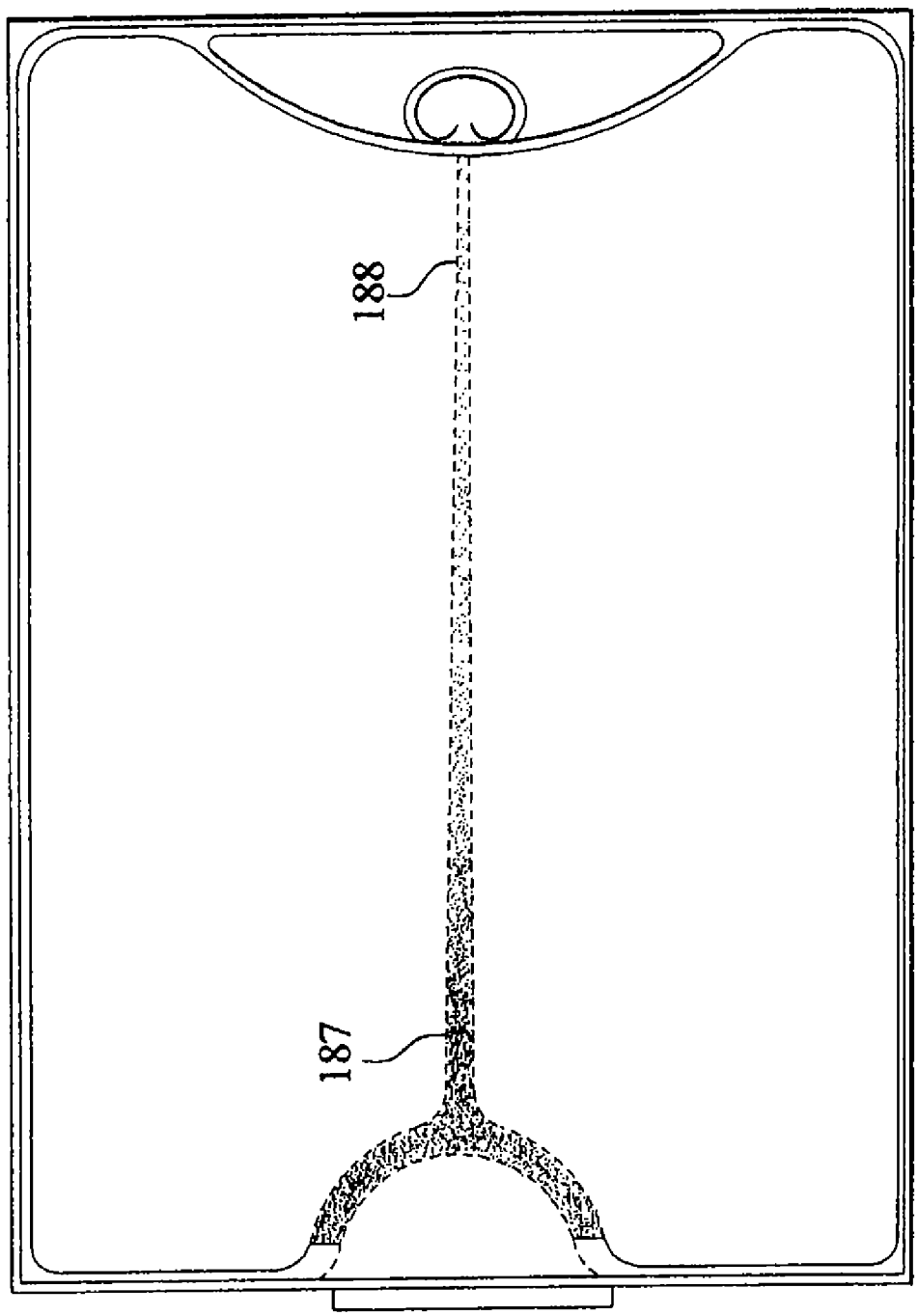
FIG. 23 is a plan view of a peel seal having a width that varies along the length of the seal.

It is also possible to vary the peel seal activating force along the length of the peel seal by varying the width of the seal along its length as shown in FIG. 23. Wider seal portions 187 will activate at higher forces than thinner sections 188. In the embodiment of FIG. 23, the wider seal portion 187 is positioned proximate the administration port and the weaker seal portion 188 is positioned distal from the administration port to ensure that mixing of the contents of the chambers by activating the thin sections 188 occurs prior to activating the wider seal portion 187.

It is also possible to vary the peel seal strength by varying the sealing temperature along the length of the peel seal with the strength of the peel seal increasing with increasing temperature, provided of course the temperature is not so high to damage the film.

Figure 24:
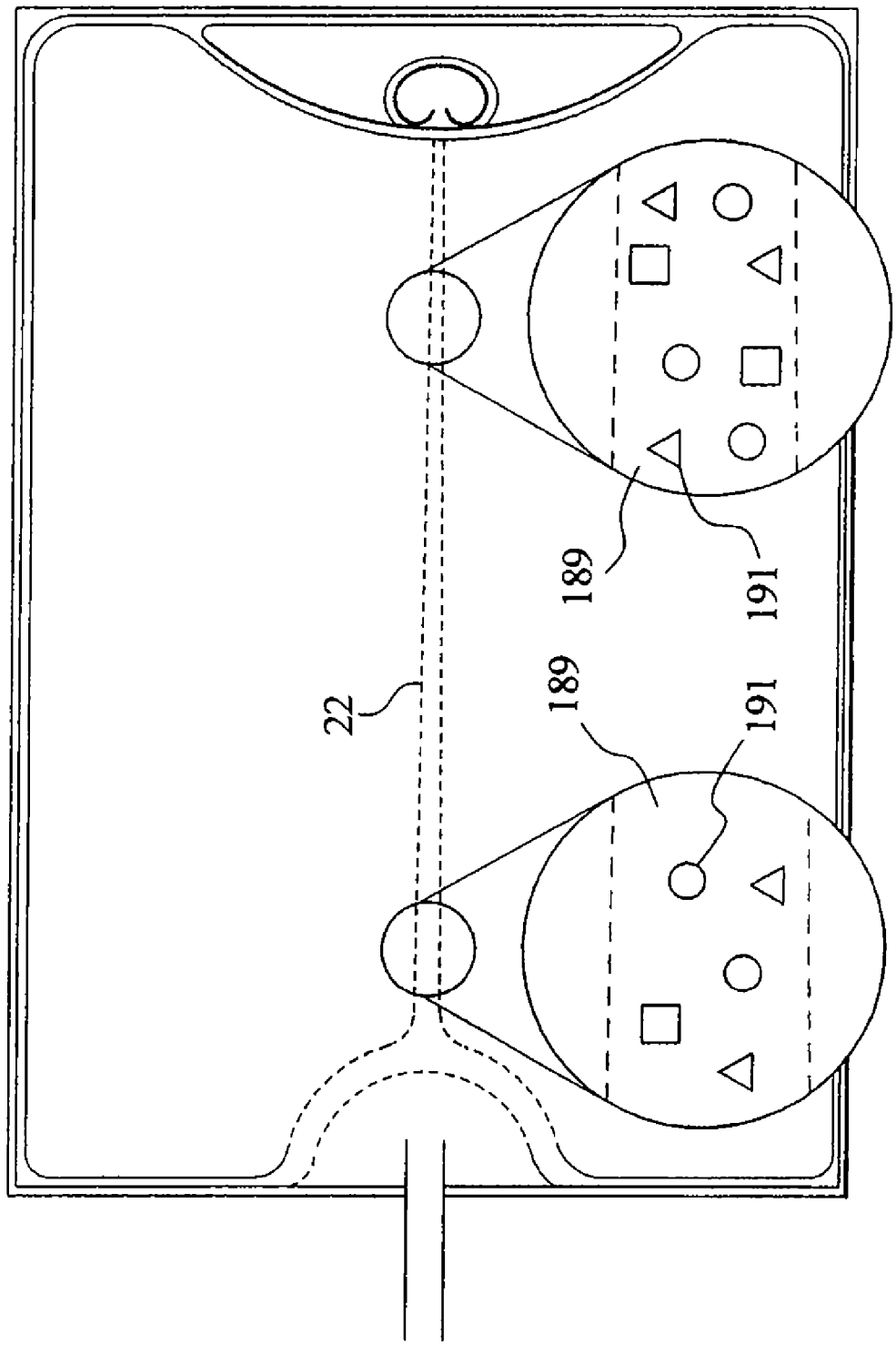
FIG. 24 is an exploded view of a peel seal having a texture.

In yet another embodiment shown in FIG. 24, the peel seal is created with a textured sealing die to create a pattern 189 on the surface of the sidewalls along the peel seal. The pattern 189 has individual elements 191. The size, shape, texture and density of the individual elements can impact the strength of the peel seal. The greater the height or depth of the elements the weaker the peel seal strength. The higher the density per unit area of the elements the lower the peel seal strength. The elements can be protuberances extending from the planar surface of the sidewall or can be indentations extending from the planar surface in a direction opposite from the protuberances. The pattern shown in FIG. 24 has an increasing density of elements with increasing distance from the closure assembly. This is to ensure peel seal activation first occurs at a location remote from the closure assembly to ensure mixing prior to delivering the mixed contents to the patient.

Closure Assemblies

FIGS. 1 and 2 show closure assembly 15 includes the conduit 30 having an inlet 32 and an outlet 34 with a closure 40. The closure can be opened or activated from fluid pressure in the chamber or can be activated from providing fluid under pressure from the outlet 34 to the inlet and through the conduit. In a preferred form of the invention, the closure will be positioned inside the chamber 16 and will be activated by fluid in the chamber. This technique of activating uses fluid flowing along a pathway other than the pathway 31 of the conduit.

In a preferred form of the invention (FIG. 25), the conduit is an assembly of a membrane tube 200 concentrically mounted within a port tube 190. The port tube/membrane tube assembly has a portion of the port tube extending into the chamber 16 and a portion of the membrane tube extending outward of the end seam outside the container 10. The sidewalls 12, 14 are attached to an outer surface of the port tube typically by heat sealing.

In a preferred form of the invention, the port tube 190 is a multilayered structure and more preferably has a first layer 192 and a second layer 194. The first layer 192 should be of a non-PVC containing material that is capable of being sealed to the sidewalls 12, 14 of the container 10, and preferably sealed using radio frequency sealing techniques, but other techniques such as sonic welding, heat transfer induction sealing and the like could be used without departing from the scope of the present invention. In a preferred form of the invention, the first layer 192 is a polymer blend of: (a) from about 25% to about 50% by weight and more preferably from about 30% to about 40% by weight, of the first layer a first polyolefin selected from the group consisting of propylene containing polymers, (b) from about 0% to about 50% by weight, and more preferably from about 5% 40% by weight, of the first layer a second polyolefin of an α-olefin containing polymer or copolymer and more preferably is an ethylene and α-olefin copolymer; (c) from about 0% to about 40% by weight, and more preferably from about 10% to about 40% by weight, of the first layer a radio frequency susceptible polymer selected from the group consisting of polyamides, ethylene acrylic acid copolymers, ethylene methacrylic acid copolymers, polyimides, polyurethanes, polyesters, polyureas, ethylene vinyl acetate copolymers with a vinyl acetate comonomer content from 18% to 50% by weight of the copolymer, ethylene methyl acrylate copolymers with methyl acrylate comonomer content from 18% to 40% by weight of the copolymer, ethylene vinyl alcohol with vinyl alcohol comonomer content from 15% to 70% by mole percent of the copolymer; and (d) from about 0% to about 40% by weight, and more preferably from 10% to about 40% by weight, of the first layer of a thermoplastic elastomer.

One particularly suitable blend for the port tube 190 first layer 192 is a four component blend having by weight the following components: from about 10% to about 40% and more preferably 30% of a dimer fatty acid polyamide, from about 0% to about 50% and more preferably from about 0% to about 10% of an ultra low density polyethylene, from about 25% to about 50% and more preferably from about 30% to about 40% of a polypropylene and from about 10% to about 40% and more preferably 30% styrene-ethylene-butylene-styrene block copolymer with maleic anhydride functionality.

The second layer 194 of the port tube 190 is of a non-PVC containing material that is capable of being solvent bonded to the membrane tube 200. In a preferred form of the invention, the second layer 194 is a multiple component blend of the following components by weight: from about 25% to about 55% and more preferably from 33%-52% of a thermoplastic elastomer, from about 20% to about 45% and more preferably from about 25% to about 42% of a polyester polyether block copolymer, from about 0% to about 15% and more preferably from about 5% to about 12% by weight of the second layer an ethylene copolymerized with vinyl lower alkyl esters and preferably vinyl acetate, from about 0% to about 10% by weight and more preferably from about 1% to about 5% by weight of the second layer of a propylene containing polymer and from about 0% to about 35% by weight of a polymer selected from the group consisting of acrylonitrile butadiene styrene (ABS) block copolymer, styrene ethylene butylene copolymer, styrene acrylonitrile copolymer and cyclic olefin or bridged polycylic olefin containing polymers.

One particularly suitable blend of the second layer 194 of the port tube is a five-component blend having from about 33% to about 35% SEBS (Kraton 1660), from about 25% to about 29% polyester polyether block copolymers (Hytrel), from about 5% to about 9% EVA, from about 1% to about 3% polypropylene and from about 28% to about 32% ABS.

Another suitable blend of the second layer 194 of the port tube is a four-component blend having from about 48% to about 52% SEBS, from about 36% to about 42% polyester polyether block copolymer, from about 8% to about 12% EVA and from about 1% to about 4% polypropylene.

Figure 25:
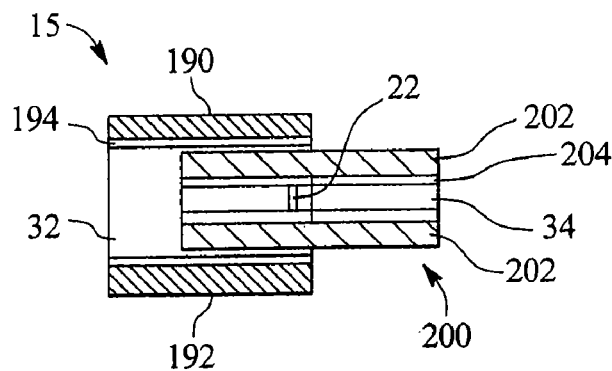
FIG. 25 is a cross-sectional view of a closure assembly.

As shown in the FIG. 25, the first layer 192 has a thickness greater than the second layer 194. In a preferred form of the invention the first layer will have a thickness of from about 15 mils to about 40 mils and more preferably from about 20 mils to about 30 mils. The second layer 194 will have a thickness from about 2 mils to about 12 mils and more preferably from about 5 mils to about 10 mils.

The membrane tube 200 should be fabricated from a non-PVC containing material and should be capable of being bonded, preferably using solvent bonding techniques, to the port tube 190. In a preferred form of the invention, the membrane tube 200 is a multilayered structure. The membrane tube 200 has an outer layer 202 and an inner layer 204. The outer layer 202 is of a material selected from the same materials as set forth for the second layer 194 of the port tube. Likewise, the inner layer 204 of the membrane tube 200 is selected from the same materials as the first layer 192 of the port tube 190.

A particularly suitable inner layer of the membrane tube is a four-component blend by weight of the inner layer 204 that slightly varies from the most preferred first layer of the port tube. The components are by weight of the inner layer 204 as follows: 40% polypropylene, 40% ultra-low density polyethylene, 10% polyamide and 10% SEBS. It should be understood, however, that the inner layer 204 of the membrane tube could also be selected from the same components and weight percentage ranges as set forth above for the first layer of the port tube.

In a preferred form of the invention, the outer layer of the membrane tube 200 should have a thickness from about 15 mils to about 35 mils and more preferably from about 20 mils to about 30 mils. The inner layer 204 of the membrane tube 202 should have a thickness from about 2 mils to about 12 mils and more preferably from about 5 mils to about 10 mils.

Figure 26:
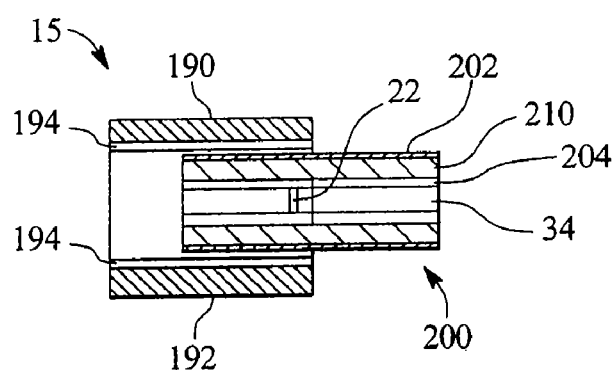
FIG. 26 is a cross-sectional view of a closure assembly.

FIG. 26 shows an alternate embodiment of the membrane tube having three layers. In addition to the outer layer 202 and inner layer 204 shown in FIG. 25, FIG. 26 shows an intermediate layer 210 interposed therebetween. The intermediate layer 210 preferably is a thermoplastic elastomer and more preferably an oil modified styrene-ethylene-butylene-styrene block copolymer sold by the Shell Chemical Company under the product designation KRATON G2705. The intermediate layer 210 can also be a blend of from about 99% to about 70% of a thermoplastic elastomer and from about 1% to about 30% of a propylene containing polymer.

In yet another preferred form of the invention (FIG. 27), the port tube 190 is a multilayered structure and more preferably has a first layer 192 and a second layer 194. The first layer 192 should be of a non-PVC containing material that is capable of being sealed to the sidewalls 12 and 14 of the container 10. In a preferred form of the invention, the first layer 192 is a polymer blend of: (a) from about 25% to about 50%, more preferably from about 30% to about 40%, by weight of the first layer a first polyolefin selected from the group consisting of polypropylene and polypropylene copolymers, (b) from about 0% to about 50%, more preferably from about 5% to about 40%, by weight of the first layer a second polyolefin of an $\alpha$-olefin containing polymer or copolymer and more preferably is an ethylene and $\alpha$-olefin copolymer; (c) from about 0% to about 40%, more preferably from about 10% to about 40% of the first layer a radio frequency susceptible polymer selected from polyamides, ethylene acrylic acid copolymers, ethylene methacrylic acid copolymers, polyimides, polyurethanes, polyesters, polyureas, ethylene vinyl acetate copolymers with a vinyl acetate comonomer content from 12% to 50% by weight of the copolymer, ethylene methyl acrylate copolymers with methyl acrylate comonomer content from 12% to 40% by weight of the copolymer, ethylene vinyl alcohol with vinyl alcohol comonomer content from 12% to 70% by mole percent of the copolymer; and (d) from about 0% to about 40%, more preferably from about 10% to about 40% of a thermoplastic elastomer by weight of the first layer.

The second layer 194 of the port tube 190 is of a non-PVC containing material that is capable of being solvent bonded to the membrane tube 200. In a preferred form of the invention, the second layer 194 is a thermoplastic elastomer or a blend of thermoplastic elastomers in an amount by weight of from about 80% to about 100% and a propylene containing polymer from about 0% to about 20% by weight of the second layer 194. It is also desirable, but optional, that the second layer 194 softens slightly at autoclave temperatures so that when the port tube and membrane tube assembly is steam sterilized, the port tube more tightly adheres to the membrane tube.

Figure 27:
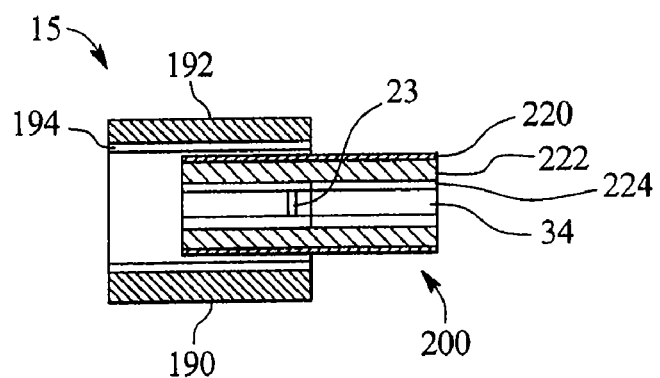
FIG. 27 is a cross-sectional view of a closure assembly.

As shown in FIG. 27, the first layer 192 has a thickness greater than the second layer 194. In a preferred form of the invention the first layer will have a thickness of from about 15 mils to about 40 mils and more preferably from about 20 mils to about 30 mils. The second layer will have a thickness from about 2 mils to about 10 mils and more preferably from about 3 mils to about 7 mils.

The membrane tube 200 should be fabricated from a non-PVC containing material and should be capable of being bonded to the port tube 190, preferably using solvent bonding techniques. Solvent bonding is well known in the art. Solvent bonding typically includes applying a solvent to a polymeric material to partially dissolve the polymer. While in this dissolved state the dissolved polymer material is placed in contact with a material, such as another polymer, that the polymeric material is to be bonded to. Suitable solvents for solvent bonding of the materials of the present invention include at least the following solvents: cyclohexane, cyclohexanone, toluene, tetrahydofuran, cumene, xylenes, diethyl benzene, decalin, tetralin and amyl benzene to name a few.

Accordingly, to solvent bond the membrane tube 200 to the port tube 190, a portion of the membrane tube 200 that is to be in contact with the port tube is exposed to the solvent, typically by dipping the relevant portion of the membrane tube into the solvent. Then the membrane tube 200 is press-fitted into the port tube where a strong bond is formed.

In a preferred form of the invention, the membrane tube 200 is a multilayered structure having an outer layer 220, a core layer 222 and an inner layer 224. In a preferred form of the invention, the outer layer 220 is a polymer blend of: (a) from about 0% to about 60%, more preferably from about 20% to about 55% and most preferably from about 30% to about 50%, by weight of the outer layer of a polyolefin and (b) from about 40% to about 100%, more preferably from about 45% to about 80% and most preferably from about 50% to about 70%, by weight of the outer layer of a thermoplastic elastomer.

Also, in a preferred form of the invention the core layer 222 is a polymer blend of: (a) from about 35% to about 100%, more preferably from about 50% to about 90% and most preferably 70% to about 90%, by weight of the core layer of a thermoplastic elastomer and (b) from about 0% to about 65%, more preferably from about 10% to about 50% and most preferably from about 10% to about 30%, by weight of the core layer of a polyolefin.

Also, in a preferred form of the invention, the inner layer 224 is a polymer blend of: (a) from about 25% to about 55%, more preferably from about 25% to about 40%, by weight of the inner layer a polyolefin; (b) from about 0% to about 50%, more preferably from about 0% to about 40% and most preferably 0% to about 20%, by weight of the inner layer a polyolefin selected from $\alpha$-olefin containing polymers or copolymers and more preferably is an ethylene and $\alpha$-olefin copolymer; (c) from about 0% to about 40% by weight, more preferably from about 15% to about 40%, of the inner layer a radio frequency susceptible polymer selected from polyamides, ethylene acrylic acid copolymers, ethylene methacrylic acid copolymers, polyimides, polyurethanes, polyesters, polyureas, ethylene vinyl acetate copolymers with a vinyl acetate comonomer content from 12% to 50% by weight of the copolymer, ethylene methyl acrylate copolymers with methyl acrylate comonomer content from 12% to 40% by weight of the copolymer, ethylene vinyl alcohol with vinyl alcohol comonomer content from 12% to 70% by mole percent of the copolymer; and (d) from about 0% to about 40%, more preferably from about 15% to about 40%, by weight of the inner layer of a thermoplastic elastomer.

In a preferred form of the invention the outer layer 220 will have a thickness from about 3 mils to about 15 mils and more preferably from about 3 mils to about 10 mils. The core layer 222 will have a thickness from about 10 mils to about 35 mils and more preferably from about 10 mils to about 30 mils. The inner layer 224 will have a thickness from about 3 mils to about 15 mils and more preferably from about 5 mils to about 10 mils.

Medication Port

Figure 28:
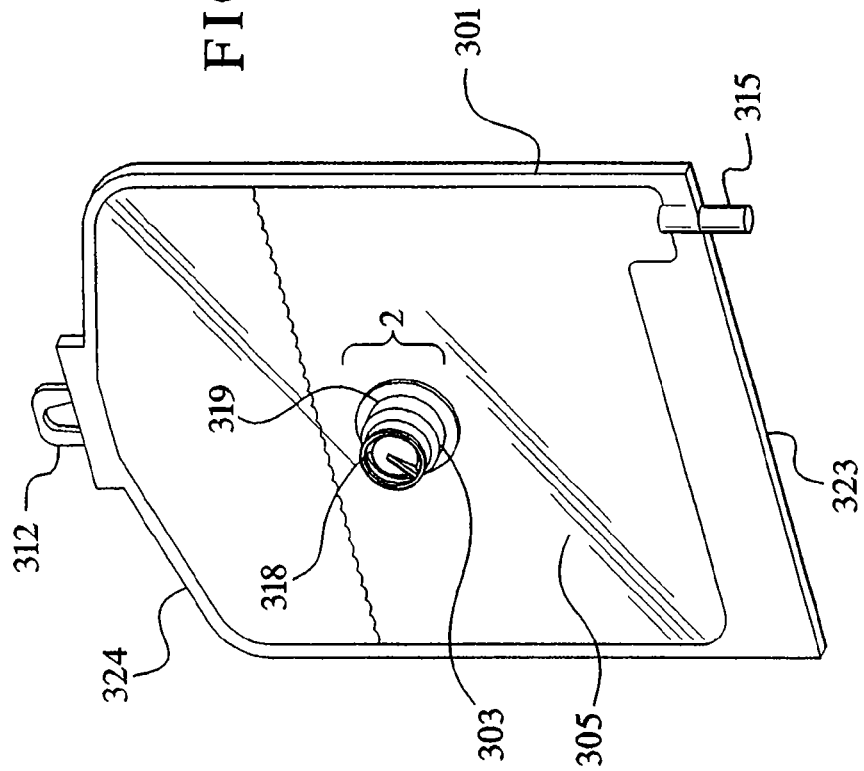
FIG. 28 is a perspective view of a container having an administration port.

FIG. 28 generally illustrates a perspective view of a container 301 having a first end 323 and a second end 324. The container 301 may be peripherally sealed and may have a liquid 305 or other solution in an interior of the container 301. The container 301 may have a port 302 having a first end 318 and a second end 319. The container 301 is illustrated in a position as is common in actual use. More specifically, the container 301 may be positioned up-right and may have the medication port 302 elevated above an administration port 315 in actual use. Additionally, a strap 312 for, for example, a hook may be provided to hang the container 301.

Figure 29:
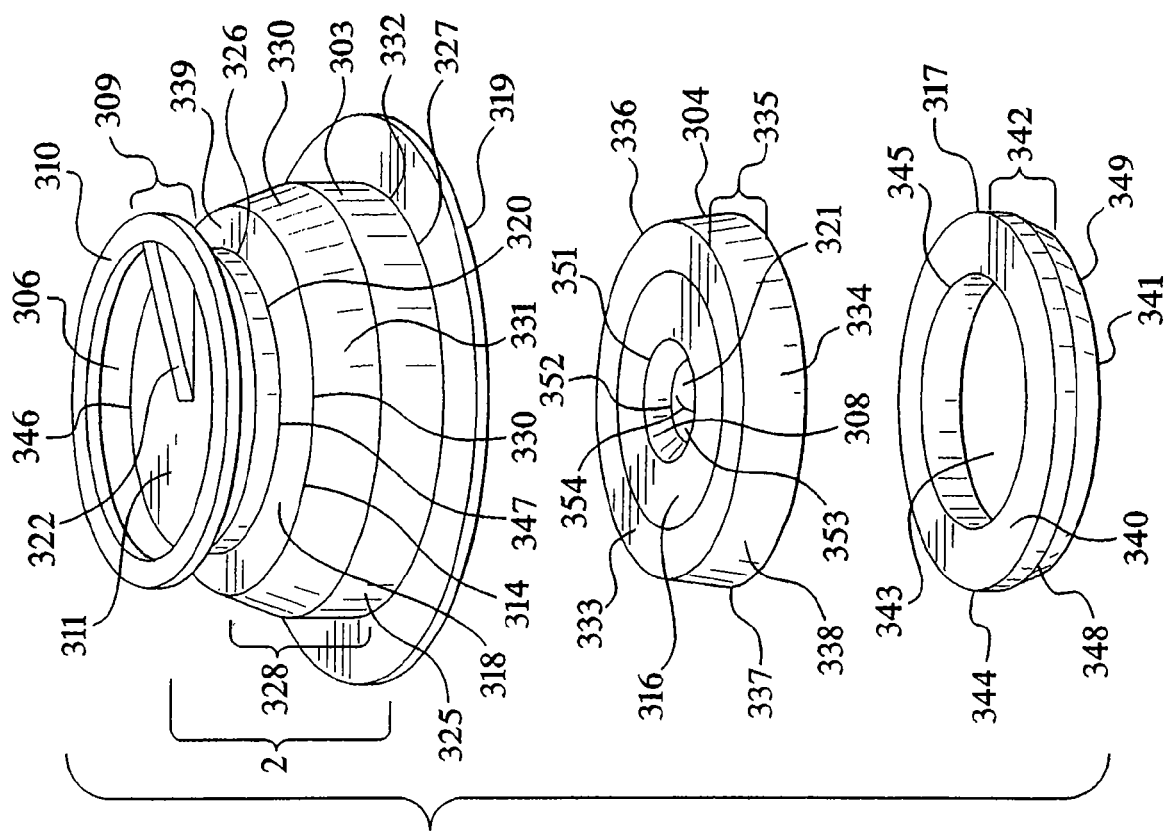
FIG. 29 is an exploded isometric view of an administration port.

Referring now to FIG. 29, the port 302 may have a housing 303 which may have a wall 325. Preferably, the port 302 is a medication port through which a medicament may be added or a solution may be removed from the container 301. The housing 303 and the wall 325 may be constructed from, for example, rubber, plastic or any other material generally known to those skilled in the art. Additionally, the housing 303 may be constructed of rigid polypropylene which may reduce risk of a needle 307 (FIG. 32) puncturing the wall 325. Further, the housing 303 may be constructed using gamma-grade materials which are approved to withstand gamma irradiation prior to sterilization as a final stage of the manufacturing process. Gamma-grade materials allow for "pre-sterilization" and reduction in autoclaving exposure time.

As illustrated in FIG. 29, the wall 325 may be circular. The wall 325 of the housing 303 may have a first end 326 and a second end 327. The second end 327 of the wall 325 may be integrally formed with the second end 319 of the medication port 302. Additionally, the first end 326 of the wall 325 may be integrally formed with a cap 309 wherein the cap 309 may be separated from the first end 326 which will be described in further detail hereinafter.

The first end 326 of the wall 325 may also have a lip 339 which protrudes inward toward a center of the housing 303. The lip 339 may be in contact with a septum 304. The lip 339 may also secure the septum 304 within the housing 303 by friction, or, alternatively, the septum 304 may be sealed to the lip 339. The lip 339 of the wall 325 may have an inner circumference 347 and an outer circumference 314 as shown in FIG. 29.

The wall 325 may have a height 328 and may have a first circumference 330 at the first end 326 and a second circumference 332 at the second end 327. Additionally, the first circumference 330 at the first end 326 of the wall 325 may be smaller than the second circumference 332 at the second end 327 of the wall 325. The smaller circumference 330 at the first end 326 of the wall 325 may result in the wall 325 being tapered. More specifically, a taper 331 may result in the wall 325 tilting inward toward the center of the housing 303.

Figure 30:
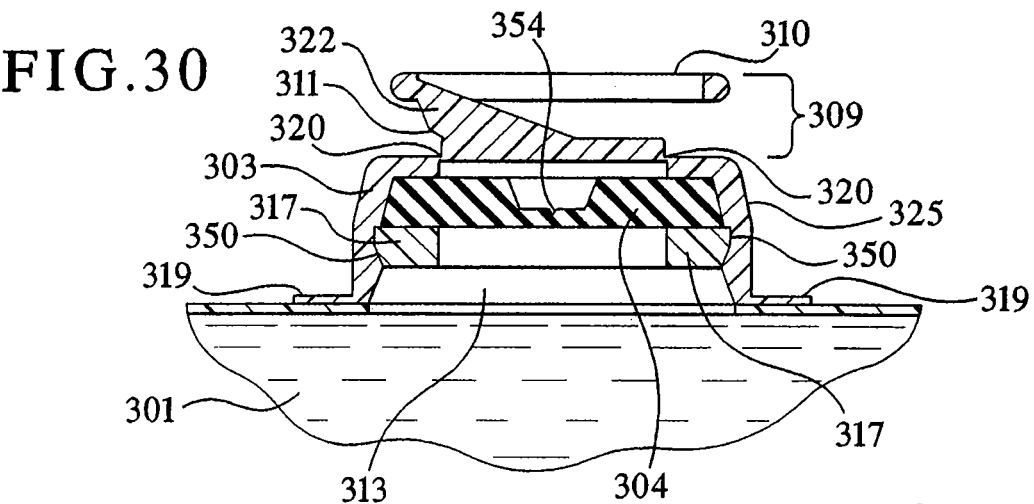
FIG. 30 is a section view of a cap of the administration port.

The septum 304 of the medication port 302 may be located within the wall 325 of the housing 303. Additionally, the septum 304 may be in contact with an inner wall 350 of the housing 303 as shown in FIG. 30.

The septum 304 may be constructed from, for example, rubber, plastic or any other material generally known to those skilled in the art. Additionally, the septum 304 may be constructed of a polyisoprene material which may allow for the septum 304 to re-seal after puncturing the septum 304 by, for example, the needle 307.

As illustrated in FIG. 29, the septum 304 may be circular. The septum 304 may have a height 335 and may have a first circumference 336 and a second circumference 337. Additionally, the septum 304 may have a first end 333 and a second end 334. The first circumference 336 at the first end 333 of the septum 304 may be smaller than the second circumference 337 at the second end 334. The smaller circumference 336 at the first end 333 may result in the septum 304 being tapered. More specifically, a taper wall 338 may result as shown in FIG. 29 wherein an opening at a top side of the septum 304 is greater than at a center of the septum 304.

The first end 333 of the septum 304 may be in contact with the lip 339 of the wall 325. The lip 339 may secure the septum 304 in place within the housing 303 and may provide a liquid-tight fit between the septum 304 and the wall 325 of the housing 303.

The septum 304 may also have a target area 316 which may assist a health-care provider or other person with insertion of, for example, the needle 307 into the septum 304. Of course, a cannula or other object may be used to pierce-the septum 304. The target area 316 may also be colored, for example, red, to contrast with the color, for example, black, of the housing 303. Use of different colors may result in the target area 316 being more visible and/or distinguishable to the health-care provider or other person.

As further illustrated in FIG. 29, a recess 321 may be located within the target area 316 of the first end 333 of the septum 304. The recess 321 may assist the health-care provider or other person by providing a reduced resistance location to insert the needle 307 through the septum 304. The target area 316 may also have a slit 354 instead of, or in addition to, the recess 321.

The recess 321 may be formed by an internal wall 308 in the target area 316 of the septum 304. More specifically, the wall 308 may have a first circumference 351 at the first end 333 of the septum and a second circumference 352 at a valley 353 within the septum 304. The first circumference 351 at the first end 333 of the septum 304 may be greater than the second circumference 352 at the valley 353 in the septum 304. The difference in the circumferences of the internal wall 308 may result in the internal wall 308 being tapered.

The health-care provider or other person may puncture the septum 304 to establish fluid communication with the liquid 305 in the container 301. A support ring 317 may support the septum 304 when an object, for example, the needle, is pressed down upon the septum 304. As illustrated in FIG. 29, the support ring 317 may resemble, for example, a ring.

More specifically, when the health-care provider or other person inserts an object through the septum 304, pressure is created on the septum 304. The support ring 317 may allow pressure to be diverted from the outer periphery of the septum 304 onto the support ring 317. As a result, the septum 304 may be able to withstand a greater pressure with the support ring 317 than without the support ring 317. The support ring 317 may be constructed from, for example, rubber, plastic or any other material generally known to those skilled in the art.

The support ring 317 may be circular and may have a first outer circumference 344, a second outer circumference 349 and an inner circumference 345. Additionally, the support ring 317 may have a first end 340 and a second end 341. The first outer circumference 344 may be at the first end 340 and a second outer circumference 349 may be at the second end 341. The first outer circumference 344 may be greater than the second outer circumference 349. As a result, the support ring 317 may taper downward. More specifically, the support ring 317 may have a taper 348. The first outer circumference 344 and the second outer circumference 349 of the support ring 317 may be in contact with the inner wall 350 of the housing 303 as shown in FIG. 30.

The support ring 317 may also have a height 342 which may be smaller than the height 328 of the wall 325. The inner circumference 345 of the support ring 317 may form a hollow interior area 343 through which the needle 307 or other object may extend after piercing the septum 304.

The first end 340 of the support ring 317 may be in contact with the second end 334 of the septum 304. Additionally, the second end 341 of the support ring 317 may be in contact with a lip 313 on the container 301.

The housing 303 may also have a cap 309 that may be constructed from, for example, rubber, plastic or any other material generally known to those skilled in the art. The cap 309 of the housing 303 may have a cover 311 having a circumference 346. The cap 309 may also have a ring handle 310. As illustrated in FIG. 29, the cover 311 and the ring handle 310 may be circular. The ring handle 310 of the cap 309 may have a hollow opening 306 through which a user may insert, for example, a finger or hook.

The cover 311 of the cap 309 may also have a line of separation 320. The line of separation 320 may be a perforation, a score line or other line of weakness formed between the cover 311 and the lip 339 of the wall 325. The line of separation 320 may be formed at the circumference 346 of the cover 311. More specifically, the line of separation 320 may provide a circumferential point at which the cover 311 may be removed from a remainder of the housing 303.

The cover 311 may be integrally formed with the ring handle 310 by a connector 322 as generally shown in FIG. 29. The connector 322 may be secured to the cover 311 and the ring handle 310 so that a pulling force may break the line of separation 320.

FIG. 30 illustrates an embodiment of the medication port 302 of the present invention with the cap 309 secured to the wall 325 of the housing 303. More specifically, FIG. 30 illustrates the medication port 302 prior to removal of the cap 309.

When the cap 309 is on the housing 303, the cap 309 may protect the septum 304 and may create a sterile environment for the septum 304 by sealing the septum 304 from the surrounding environment. More specifically, when the cap 309 is secured to the wall 325 of the housing 303, dust, pathogens and other harmful substances may not access the septum 304 located within the housing 303.

Additionally, when the cap 309 is in the sealed position, the septum 304 may be protected from physical damage. The cap 309 may prevent accidental damage that may otherwise occur to the septum 304 if the septum 304 was unprotected.

Figure 31:
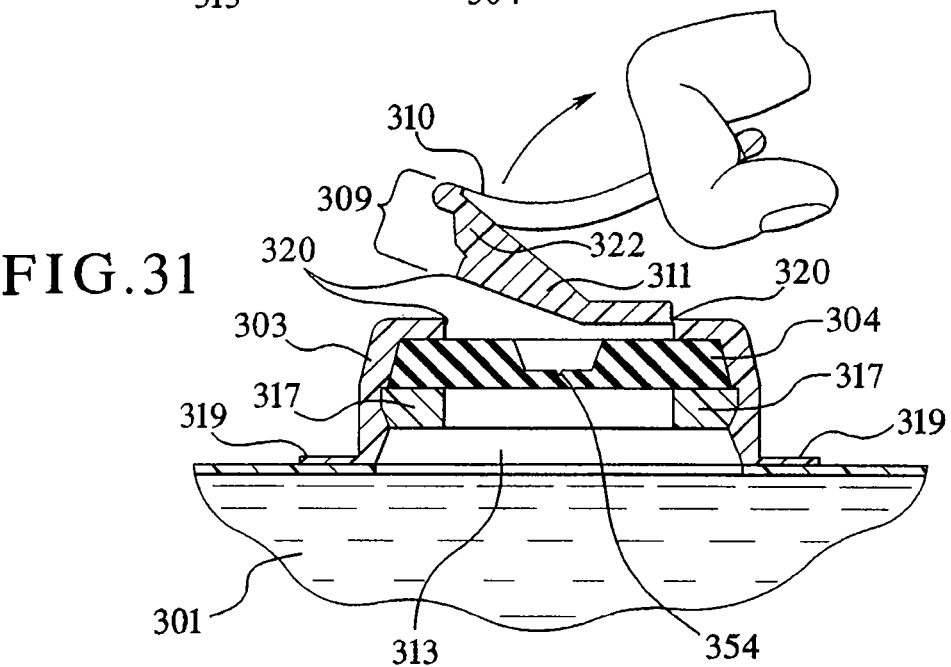
FIG. 31 is a sectional view of a user removing a cap of the administration port.

FIG. 31 illustrates an embodiment of the present invention with the cap 309 of the medication port partially removed. The ring handle 310 of the cap 309 may be lifted by, for example, a finger of a user or a hook. When the user pulls on the ring handle 310, the line of separation 320 may break and may allow the user to remove the cap 309. When the cap 309 is removed, the septum 304 may be exposed. Upon removal of the cap 309, the septum 304 may be ready for use through penetration of the septum 304 by, for example, the needle 307.

Figure 32:
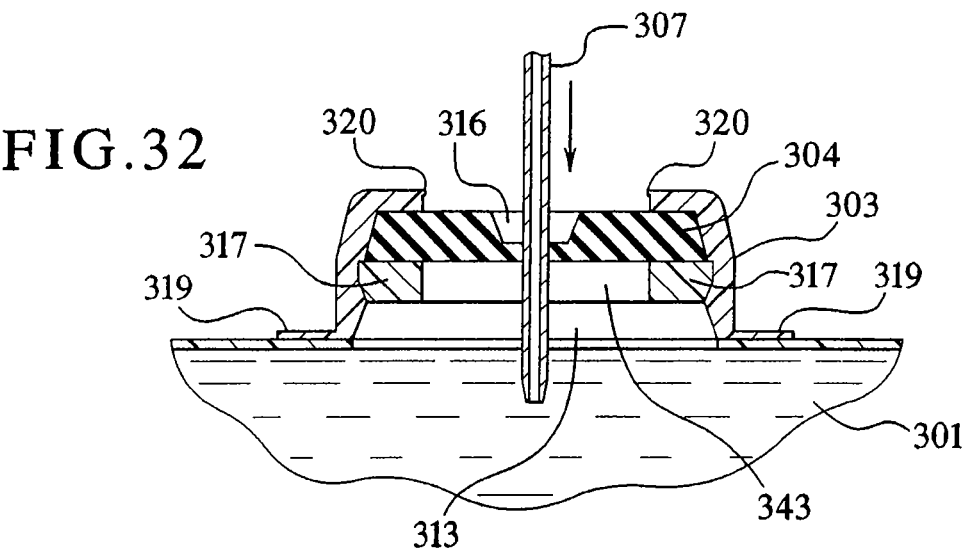
FIG. 32 is a sectional view of a needle inserted into the port.

FIG. 32 illustrates an embodiment of the medication port 302 of the present invention with the cap 309 removed from the wall 325 of the housing 303. FIG. 32 also illustrates the needle 307 inserted through the septum 304 to provide fluid communication with the liquid 305 inside the interior of the container 301.

The septum 304 may be punctured by the needle 307 or cannula (not shown). The needle 307 or other object may pierce the septum 304 through the target area 316 on the septum 304. The needle 307 or other object may then pass through the hollow interior 343 of the support ring 317. After the needle or other object is inserted into the container 301, liquid may be added or withdrawn to from the container 301 as may be required.

Access Member

Figure 33:
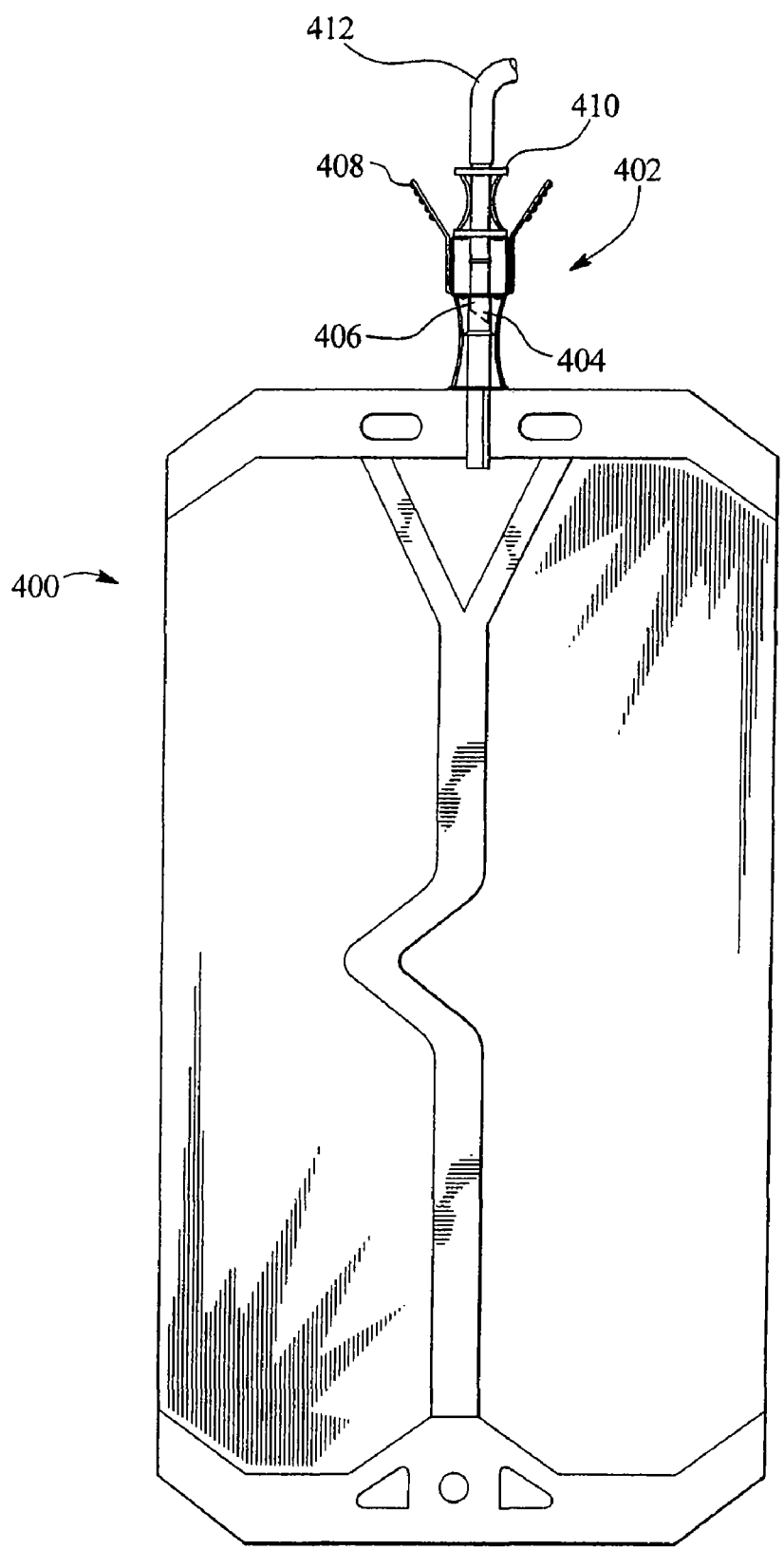
FIG. 33 is a plan view of a peel seal container with an access member in an inactivated position.
Figure 34:
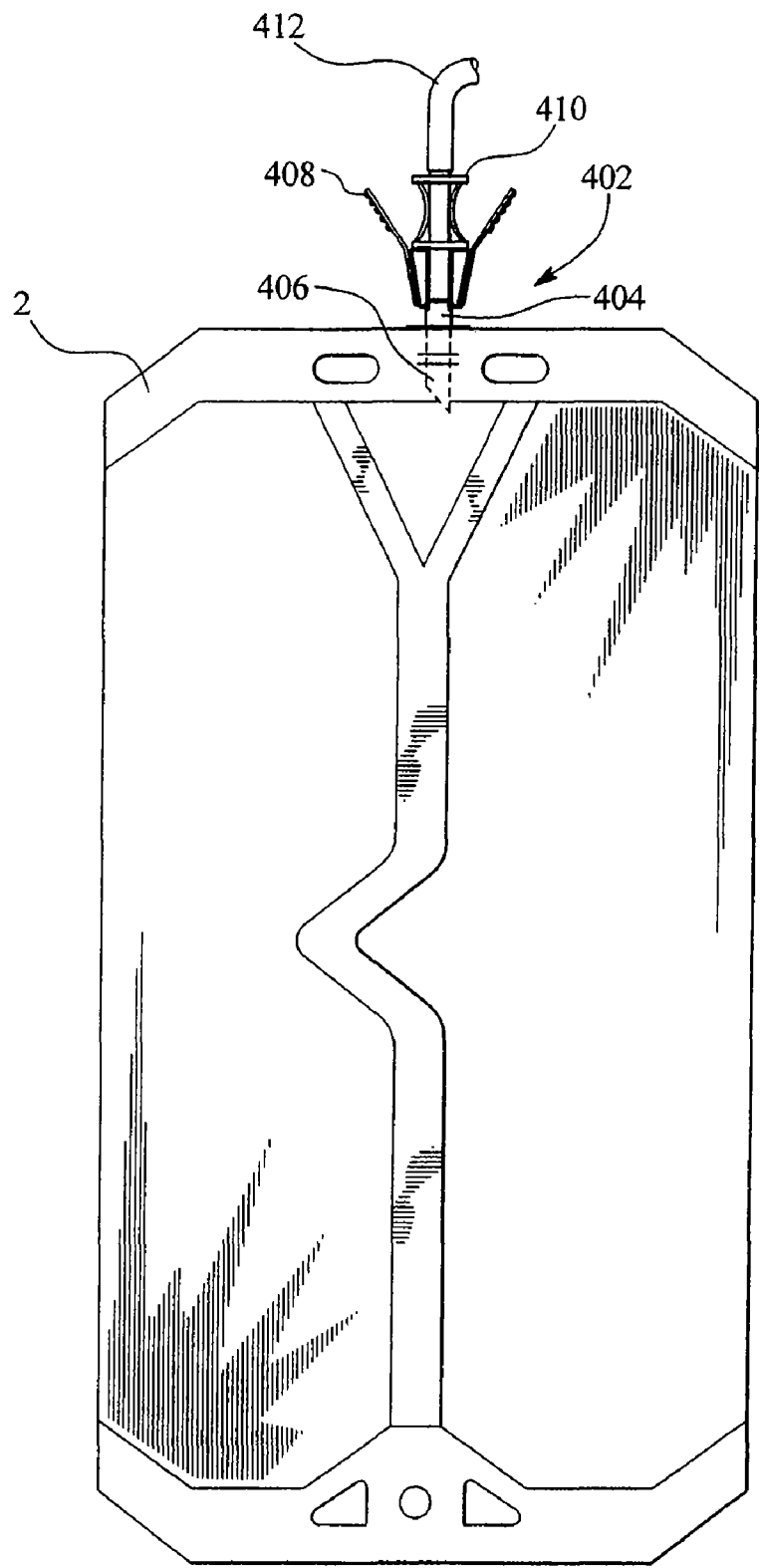
FIG. 34 is a plan view of a peel seal container with an access member in an activated position.

FIG. 33 shows a peel seal container 400 having an access device 402 associated therewith. The access member has a piercing cannula 404 defining a fluid pathway 406 therethrough, an activating member 408 to move the cannula 404 from an inactivated position where the piercing cannula 404 has not punctured a sidewall of the container (FIG. 33) to an activated position (FIG. 34) where the cannula pierces a sidewall of the container, a fluid line docking portion 410 and a tubing 412 connected to the docking portion 410. A suitable access device 402 is disclosed in U.S. Patent Docket No. DI-5805, which is incorporated in its entirety herein by reference and made a part hereof.

Figure 35:
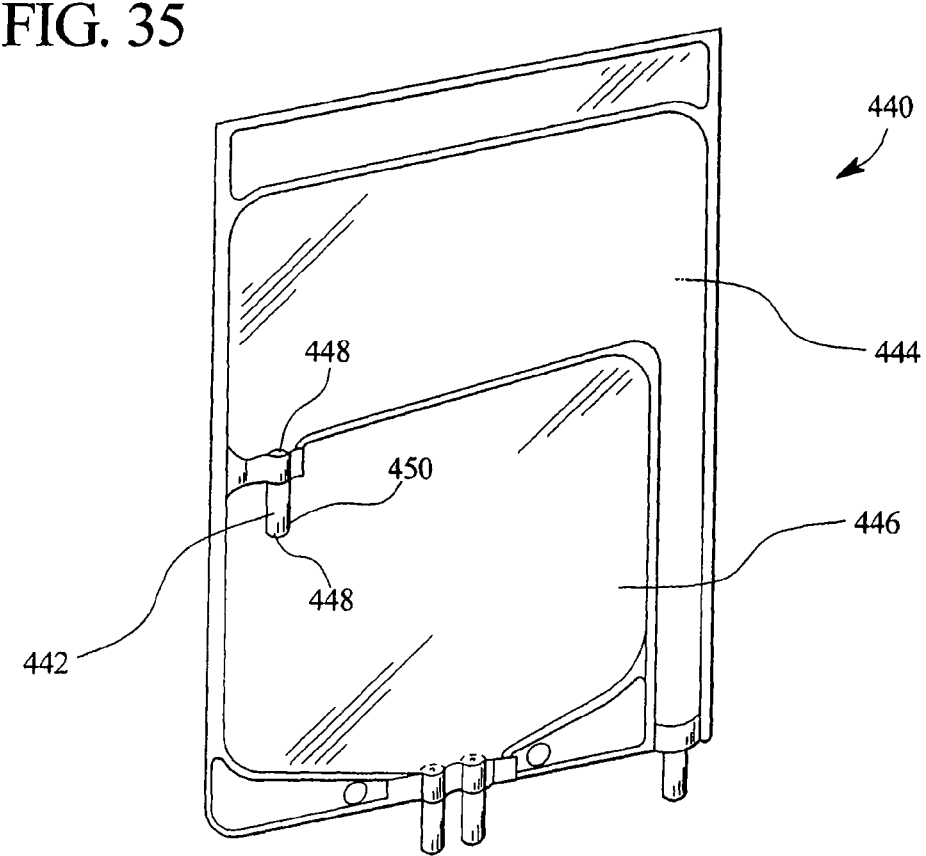
FIG. 35 is a multiple chamber container with a peel seal conduit separating two chambers of the container.

FIG. 35 shows yet another embodiment of a peel seal container 440 having a fluid conduit 442 between a first and a second chambers 444, 446. The fluid conduit 442 has opposed ends having fluid outlets 448 with a peel seal 450 formed from the opposed sidewalls being sealed over the fluid outlets 448. The top or the bottom chamber can be pressed to open the peel seal over either of the openings to allow the contents of the chambers to mix.

Using a Dual Chamber Peel Seal Container

Figure 36:
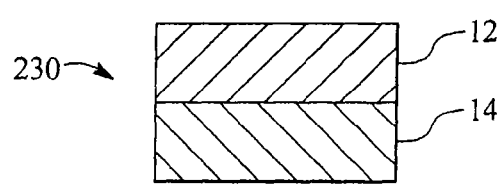
FIG. 36 is a layered structure prior to peel initiation.
Figure 37:
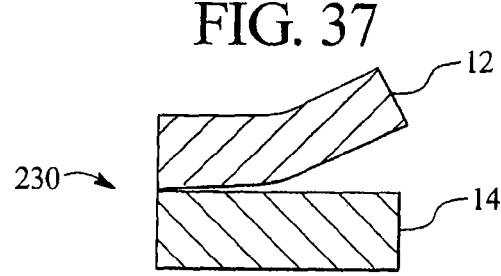
FIG. 37 is the layered structure during peeling.
Figure 38:
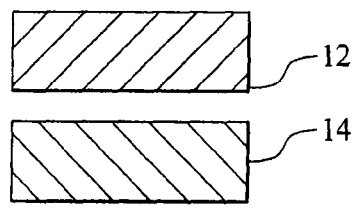
FIG. 38 is the former layered structure now completely delaminated.

FIGS. 36-38 show a sequence of activating a peel seal. FIG. 36 shows a layer structure 230 formed from the first wall having its planar surface in contact with a planar surface of the second wall to define a fully laminated state. FIG. 37 shows a portion of the first wall 12 lifting from the second wall 14 to define a partially delaminated state. Finally, FIG. 38 shows the wall 12 fully disconnected from the wall 14 to define a fully delaminated or open state.

As set forth above (FIG. 1), the first portion 40 of the peelable seal 22 has a higher peel seal activation energy than the second portion 42. To activate the container shown in FIG. 1, one need only press on one of the sidewalls to apply a fluid pressure to the peel seal 22. Upon generating sufficient pressure the second portion 42 of the peel seal delaminates thereby creating a fluid pathway from the first sub-chamber 18 to the second sub-chamber 20 thereby allowing the contents to mix. Upon adequate mixing of the components the container is pressed again to generate sufficient pressure to activate the first portion of the peel seal to open the closure to place the conduit fluid communication with the contents of the chamber.

The present invention contemplates having a second closure attached to the assembly that must be punctured or activated to draw fluid from the conduit. Such closures are well known in I.V. containers and CAPD containers, and are typically associated with fluid administration sets.

Method for Manufacturing and Filling a Dual Chamber Container

The container 10 is fabricated using standard heat sealing techniques. Separate rolled stock of the sidewall material are fed through packaging machinery where the sidewalls have peripheral edges placed in registration. Prior to sealing, the longitudinal end seams, a closure assembly 15 is inserted between the walls 12 and 14 and heat sealed in place. The peel seal 22 can be formed prior to, during or after forming the permanent seal and is preferably made using heat conduction sealing techniques. The welding die for the peel seal may have different temperatures and shapes along its length to achieve the desired peel seal.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A flowable materials container comprising: a pair of opposing sidewalls defining a chamber therebetween, interfacing portions of opposed sidewalls are sealed together along a peel seal to define at least two separate sub-chambers; and a conduit having a portion extending into the chamber and having a fluid inlet, the fluid inlet is closed by a portion of the peel seal.

2. The container of claim 1, wherein the peel seal is moveable from a closed position to an activated position.

3. The container of claim 2, wherein the peel seal is moveable from a closed position to an activated position in response to fluid pressure applied to the peel seal.

4. The container of claim 3, wherein the peel seal has a first portion proximate the inlet having a first peel seal activating force and a second portion distal from the closure having a second peel seal activating force wherein the second peel seal activating force is less than the first peel seal activating force.

5. The container of claim 1, wherein the conduit is generally circular in cross-sectional shape and has an axis that extends in a direction parallel to the peel seal.

6. The container of claim 1, wherein the conduit is generally circular in cross-sectional shape and has an axis that extends in a direction transverse to the peel seal to define an angle.

7. The container of claim 6, wherein the angle is an obtuse angle.

8. The container of claim 6, wherein the angle is an acute angle.

9. The container of claim 6, wherein the angle is approximately a right angle.

10. The container of claim 1, wherein the peel seal has a length, the peel seal having a serrated portion along at least a portion of its length.

11. The container of claim 10 wherein the serrated portion has an edge shape selected from the group consisting of a scalloped seal edge and a trapezoidal seal edge.

12. The container of claim 1, wherein the sidewalls are connected together along a permanent seal about a periphery of the container and the peel seal extends between two points on the periphery.

13. The container of claim 10, wherein the peel seal has a first edge and a second edge, and the serrated portion is located on one of the first edge or the second edge.

14. The container of claim 12, wherein the peel seal has a first edge and a second edge, and a serrated portion is located on both the first edge and the second edge.

15. The container of claim 1, wherein the serrated portion is spaced from the periphery.

16. The container of claim 12, wherein the serrated portion includes inner points, outer points, angular legs connecting the inner points and outer points, and a depth between the outer points and inner points.

17. The container of claim 12, wherein the first sidewall and second sidewall of the container form an angular joint at the inner points.

18. The container of claim 1 wherein each sidewall is a single layer structure.

19. The container of claim 1 wherein a portion of one sidewall is wrapped over an outside surface of the other sidewall.

20. The container of claim 1 wherein the peel seal has a central portion and first and second outer edges, the peel force of the edges being less than the peel force of the central portion.

21. The container of claim 1 wherein the peel seal further comprises a first peel seal portion and a second peel seal portion, the second peel seal portion having a greater separation force than the first peel seal portion.

22. The container of claim 21 wherein the peel force of the central portion is about three times less than the peel force of the edges.

23. The container of claim 21 wherein the second peel seal portion is disposed between a first area and a second area of the first peel seal portion.

24. The container of claim 21 wherein the first peel seal portion and the second peel seal portion are substantially coextensive.

* * * * *